US009926570B2

(12) United States Patent
Jin et al.

(10) Patent No.: US 9,926,570 B2
(45) Date of Patent: Mar. 27, 2018

(54) HOST CELLS AND METHODS OF USE

(71) Applicant: GlaxoSmithKline LLC, Wilmington, DE (US)

(72) Inventors: Yonghwan Jin, King of Prussia, PA (US); Yuan Zhu, King of Prussia, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 14/772,436

(22) PCT Filed: Mar. 6, 2014

(86) PCT No.: PCT/US2014/021137
§ 371 (c)(1),
(2) Date: Sep. 3, 2015

(87) PCT Pub. No.: WO2014/138371
PCT Pub. Date: Sep. 12, 2014

(65) Prior Publication Data

US 2016/0017343 A1 Jan. 21, 2016

Related U.S. Application Data

(60) Provisional application No. 61/773,329, filed on Mar. 6, 2013.

(51) Int. Cl.

| | |
|---|---|
| *C12N 15/81* | (2006.01) |
| *C12N 1/16* | (2006.01) |
| *C12P 21/02* | (2006.01) |
| *C12N 9/90* | (2006.01) |
| *C12N 9/02* | (2006.01) |
| *C12N 9/60* | (2006.01) |

(52) U.S. Cl.
CPC ........... *C12N 15/81* (2013.01); *C12N 9/0051* (2013.01); *C12N 9/60* (2013.01); *C12N 9/90* (2013.01); *C12P 21/02* (2013.01); *C12Y 108/04* (2013.01); *C12Y 304/21061* (2013.01); *C12Y 503/04001* (2013.01)

(58) Field of Classification Search
None
See application file for complete search history.

(56) References Cited

U.S. PATENT DOCUMENTS

| | | | |
|---|---|---|---|
| 5,077,204 A | 12/1991 | Brake et al. | |
| 5,501,975 A | 3/1996 | Chaudhuri et al. | |
| 5,521,093 A | 5/1996 | Lemoine et al. | |
| 5,618,690 A | 4/1997 | Chaudhuri et al. | |
| 5,965,386 A | 10/1999 | Kerry-Williams et al. | |
| 6,291,205 B1 | 9/2001 | Tuite et al. | |
| 6,361,964 B1 | 3/2002 | Kaiser et al. | |
| 6,379,924 B1 | 4/2002 | Sleep et al. | |
| 7,504,493 B2 | 3/2009 | Velculescu et al. | |
| 8,034,607 B2 | 10/2011 | Shusta et al. | |
| 8,143,026 B2 | 3/2012 | Rosen et al. | |
| 2006/0046253 A1 | 3/2006 | Nakao et al. | |
| 2007/0031851 A1 | 2/2007 | Velculescu et al. | |
| 2007/0117186 A1 | 5/2007 | Sahara et al. | |
| 2009/0123452 A1 | 5/2009 | Madison | |
| 2011/0014651 A1 | 1/2011 | Chiba et al. | |
| 2011/0129872 A1 | 6/2011 | Lim et al. | |
| 2014/0128326 A1* | 5/2014 | Cameron | C07K 14/765 514/15.2 |

FOREIGN PATENT DOCUMENTS

| | | |
|---|---|---|
| EP | 0 327 377 A2 | 8/1989 |
| EP | 0 327 377 A3 | 8/1989 |
| EP | 0 396 436 A1 | 11/1990 |
| EP | 0 467 839 A1 | 1/1992 |
| EP | 0 548 012 A1 | 6/1993 |
| EP | 0 396 436 B1 | 8/1994 |

(Continued)

OTHER PUBLICATIONS

Park et al. Effects of Trx2p and Sec23p expression on stable production of hepatitis B surface antigen S domain in recombinant *Saccharomyces cerevisiae*. 2012. Journal of Biotechnology. vol. 160, pp. 151-160.*

Baggio et al. A Recombinant Human Glucagon-Like Peptide (GLP)-1-Albumin Protein (Albugon) Mimics Peptidergic Activation of GLP-1 Receptor-Dependent Pathways Coupled With Satiety, Gastrointestinal Motility, and Glucose Homeostasis. Sep. 2004. Diabetes. vol. 53, pp. 2492-2500.*

Frand et al. The ERO1 Gene of Yeast Is Required for Oxidation of Protein Dithiols in the Endoplasmic Reticulum. Jan. 1998. Molecular Cell. vol. 1, pp. 161-770.*

Serviene et al. Influence of Kex1p and Kex2p proteases on the function of *Saccharomyces cerevisiae*. 2007. Biologija. vol. 18, No. 1, pp. 35-38.*

(Continued)

*Primary Examiner* — Channing S Mahatan

(74) *Attorney, Agent, or Firm* — Leah M. Octavio; Andrea V. Lockenour

(57) ABSTRACT

The present invention relates to genetically modified host cells, in particular yeast cells, comprising at least one isolated polynucleotide encoding a Killer Expression protease (Kex2p) or a fragment and/or variant thereof which has at least one Kex2p functional activity and at least one isolated polynucleotide encoding a Protein Disulfide-Isomerase (Pdi1) or a fragment and/or variant thereof which has at least one Pdi functional activity. Also provided herein are genetically modified host cells comprising at least one isolated polynucleotide encoding a Killer Expression protease (Kex2p) or a fragment and/or variant thereof which has at least one Kex2p functional activity, at least one isolated polynucleotide encoding a Protein Disulfide-Isomerase (Pdi1) or a fragment and/or variant thereof which has at least one Pdi1 functional activity and at least one isolated polynucleotide encoding a Endoplasmic Reticulum Oxidoreductin (Ero1) or a fragment and/or variant thereof which has at least one Ero1 functional activity.

17 Claims, 7 Drawing Sheets

(56) References Cited

FOREIGN PATENT DOCUMENTS

| | | | |
|---|---|---|---|
| EP | 0 327 377 | B1 | 6/1995 |
| EP | 0 467 839 | B1 | 8/1996 |
| EP | 0 548 012 | B1 | 9/1997 |
| EP | 0 794 254 | A2 | 9/1997 |
| EP | 0 794 254 | A3 | 1/2000 |
| EP | 0 794 254 | B1 | 8/2008 |
| WO | WO 95/23857 | A1 | 9/1995 |
| WO | WO 2006/117225 | A3 | 11/2006 |
| WO | WO 2008/045148 | A2 | 4/2008 |
| WO | WO 2009/082209 | A1 | 7/2009 |

OTHER PUBLICATIONS

Araki, et al., "Erol-α and PDIs constitute a hierarchical electron transfer network of endoplasmic reticulum oxidoreductases", *J. Cell Biol.*, vol. 202, No. 6, pp. 861-874 (2013).
Tsai, et al., *Journal of Cell Biology*, 159(2):167-216 (2002).
Gasser, et al., *Microb Cell Fact.*, 7(11) (2008).
Heiligenstein, Susanne, *Biol.*, XP55284271, 1-15 (2008).
Shin Sy, et al., *Bioprocess Biosyst Eng*, 37(6): 1065-1071 (2013).
EP Search Report, App. No. 14760330.2, dated Jul. 11, 2016.

* cited by examiner

Figure 1. Creation of Preliminary Master Cell Bank of Albiglutide producing strain. Steps from KEX2-KanMX Expression cassette PCR product to BXP10KEX2PDIERO1 Production Host are the sequential integrations of expression cassettes to construct Process IV host strain, BXP10_*KEX2*_PDI_*ERO1*. After transformation of pCID3610 plasmid, the final production clone was selected and was used in making a Preliminary Master Cell Bank (PCB).

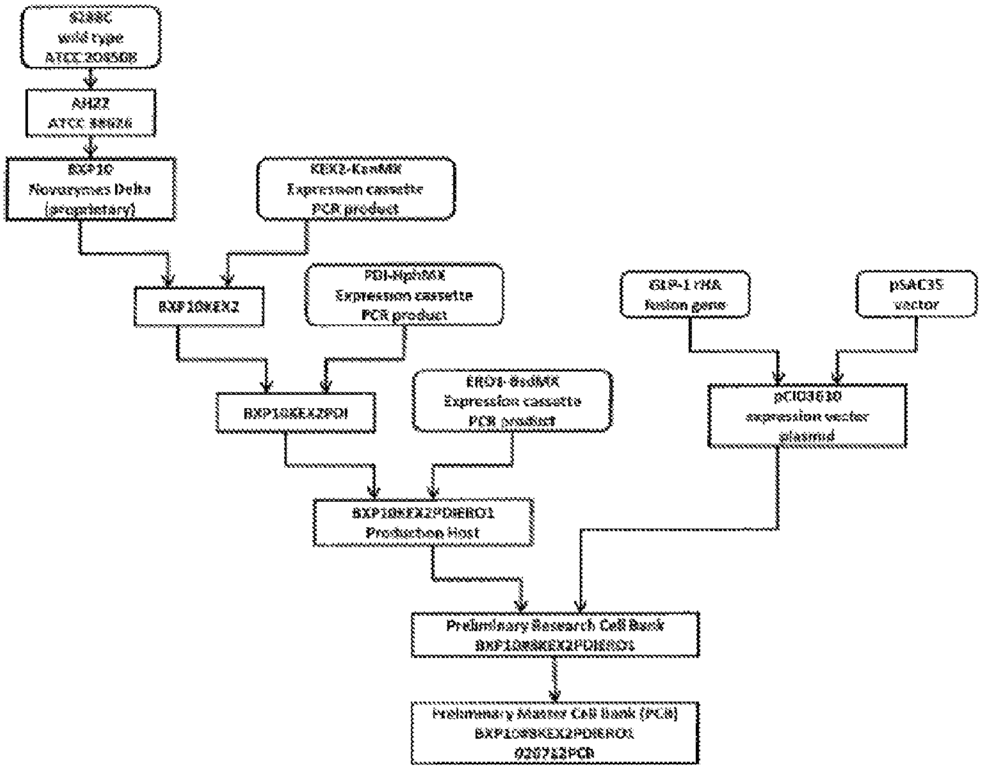

Figure 2: Southern blot analysis of *PDI1* and *KEX2* in the host strains. The endogenous *KEX2* and *PDI1* genes are located in the chromosome XIV and III, respectively, as a single copy (wild type). The target site of integration was shown below the wild type in the chromosome XII. The detecting probes for each gene are shown as solid rectangle.

**Southern Blot for *KEX2* and *PDI1***

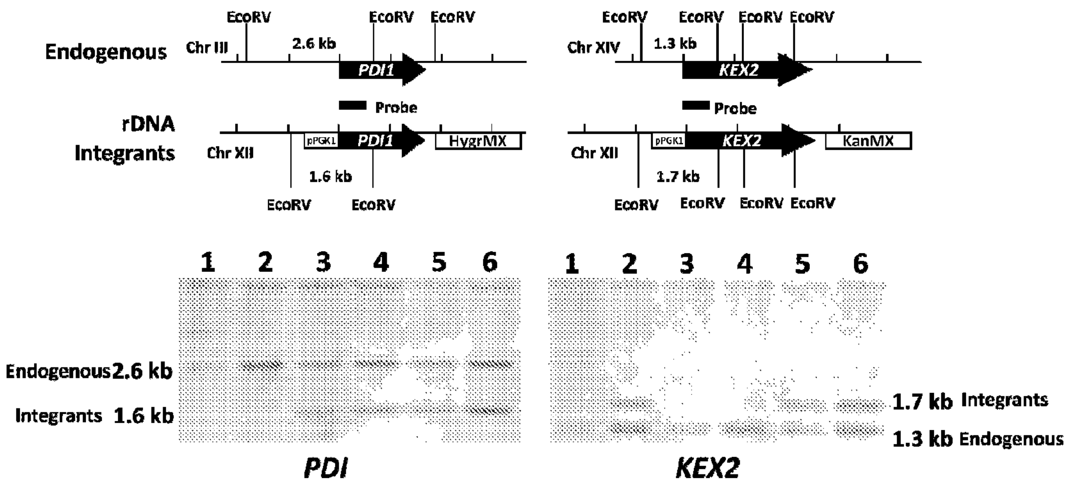

1. BXP10
2. BXP10 *nts2::KEX2*
3. BXP10 *nts2::PDI1* #1
4. BXP10 *nts2::PDI1* #2
5. BXP10 *nts2::KEX2 nts2::PDI1* #1
6. BXP10 *nts2::KEX2 nts2::PDI1* #2

Figure 3: Western blot analysis of *PDI1* and *KEX2* from the host strains. Samples in the lane, Lanes 1-5: 5 clones of BXP10-*KEX2-PDI1* strain; PDI: BXP10 overexpressing *PDI1*; *KEX2*: BXP10 overexpressing *KEX2*; and BXP10: host strain as a control. Equivalent amount of proteins were loaded.
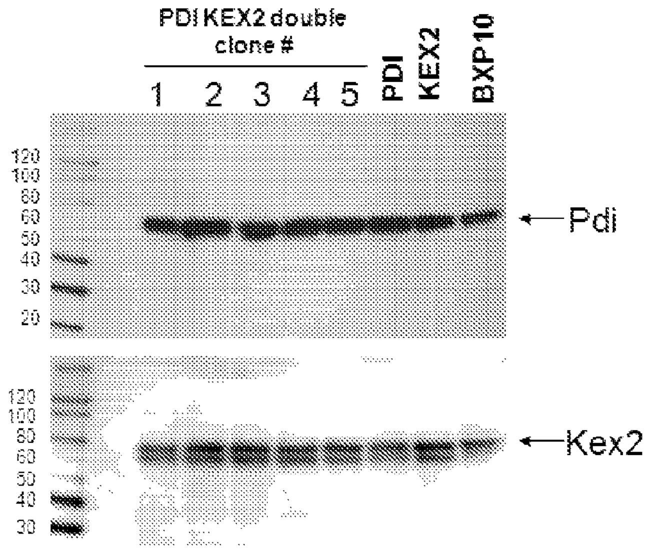

Figure 4. SDS-PAGE of 12 supernatant samples from shaking plate test. Lanes in the gel; L: SeeBlue2 prestained protein ladder (Invitrogen); RS. Reference standard of pCID3610 protein; 1-12: 12 subclones expressing pCID3610
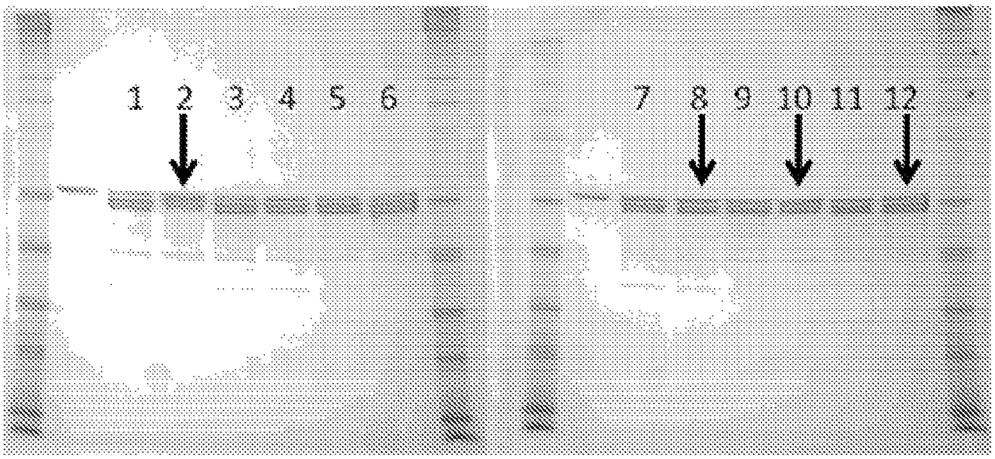

Figure 5: Analysis of titer (A) and quality (B) of pCID3610 protein produced in DasGip fermentation run. The supernatant titer yield and 6-AA levels (%) of pCID3610 protein were compared with BXP10-*KEX2-PDI1*, as a control, which is BXP10 overexpressing *KEX2* and *PDI1*.
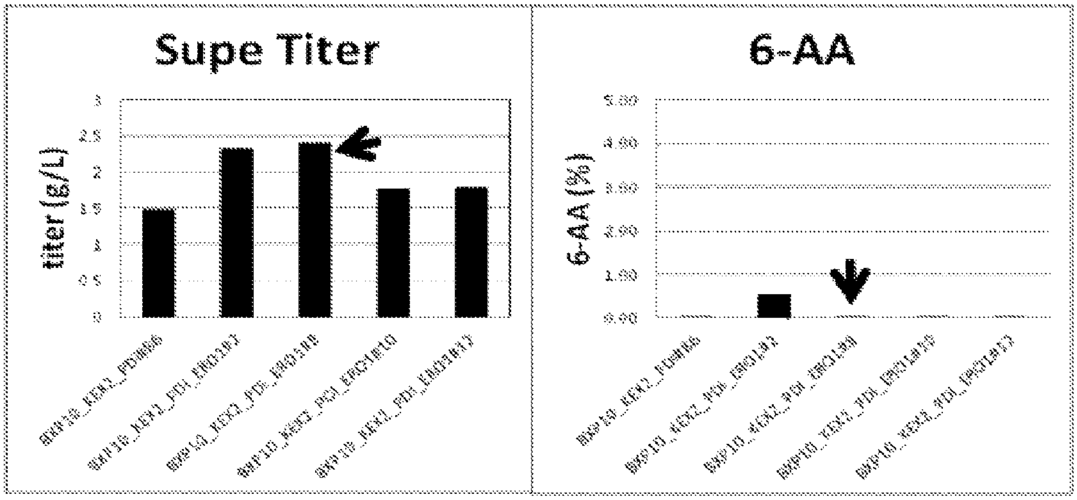

Figure 6: Growth curves generated from Research Cell Bank Vial cells.
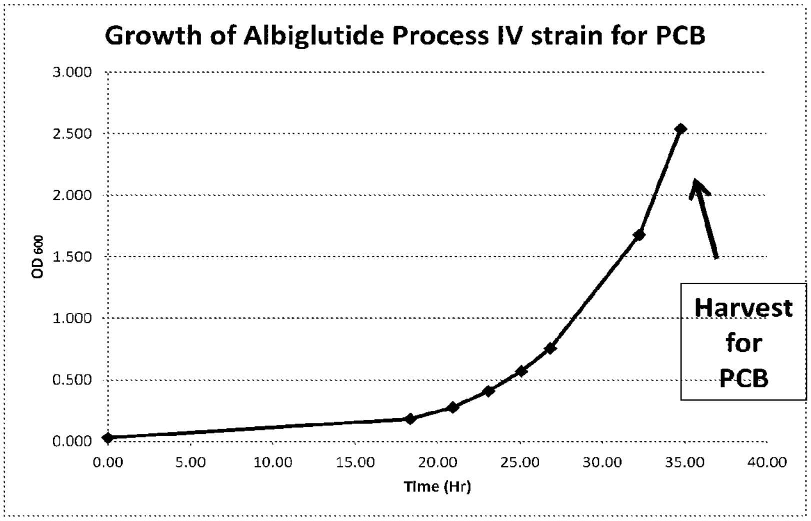

Figure 7: Growth curves generated from Pre-Master Cell Bank cells.
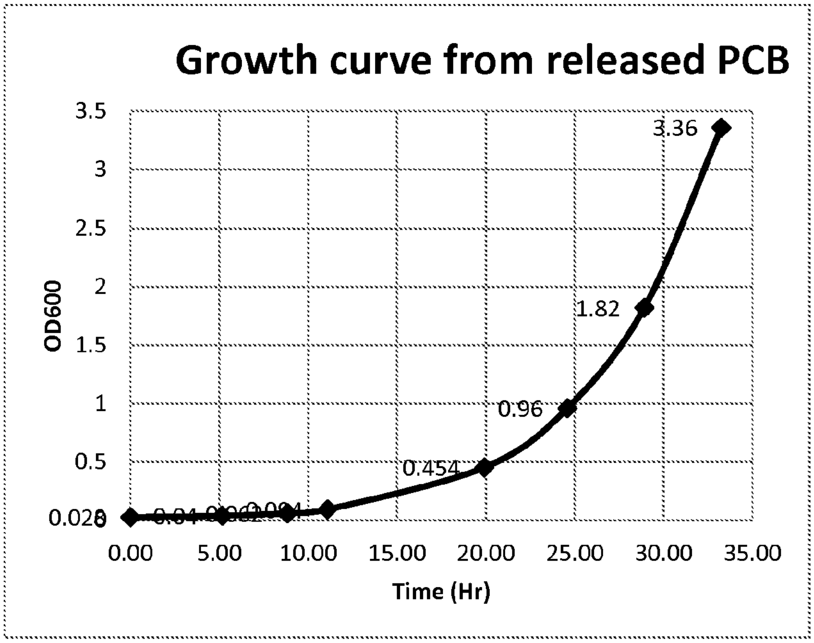

HOST CELLS AND METHODS OF USE

This application is a 371 of International Application No. PCT/US2014/021137, filed Mar. 6, 2014, which claims the benefit of U.S. Provisional Application No. 61/773,329, filed Mar. 6, 2013, which are incorporated herein in their entireties.

FIELD OF THE INVENTION

This invention is in the field of biochemical engineering. More particularly, this invention relates to genetically modified host cells and methods for producing polypeptides in them.

BACKGROUND OF THE INVENTION

Therapeutic polypeptides and proteins can be expressed in a variety of host cells including bacterial cells, *E. coli* cells, fungal or yeast cells, cells of a microorganism, insect cells, and mammalian cells. Fungal hosts such as the methylotrophic yeast *Pichia pastoris* has distinct advantages for therapeutic protein expression—e.g. it does not secrete high amounts of endogenous proteins, it has a strong inducible promoter, it can be grown in defined chemical media, and it can produce high titers of recombinant proteins (Cregg et al., *Mol. Biotech.* 16:23-52 (2000)). Yeast and filamentous fungi have both been successfully used for the production of recombinant proteins, both intracellular and secreted (Cereghino, J. L. and J. M. Cregg 2000 *FEMS Microbiology Reviews* 24(1): 45 66; Harkki, A., et al. 1989 *Bio-Technology* 7(6): 596; Berka, R. M., et al. 1992 Abstr. *Papers Amer. Chem. Soc.* 203: 121-BIOT; Svetina, M., et al. 2000 *J. Biotechnol.* 76(23): 245-251. *S. cerevisiae* is a remarkable host cell for expression of recombinant human serum albumin (HSA). However, the expression of other therapeutic polypeptides including polypeptides genetically fused with HSA faces the technical barriers of low titers of recombinant proteins.

Thus, there is a need for host cells, in particular *S. cerevisiae* strains, that are capable of producing heterologous peptides, polypeptides and/or proteins with high titers of a recombinant protein.

SUMMARY OF THE INVENTION

In one aspect of the present invention, genetically modified host cells are provided comprising at least one isolated polynucleotide encoding a Killer Expression protease (Kex2p) or a fragment and/or variant thereof which has at least one Kex2p functional activity and at least one isolated polynucleotide encoding a Protein Disulfide-Isomerase (Pdi1) or a fragment and/or variant thereof which has at least one Pdi functional activity. Also provided herein are genetically modified host cells comprising at least one isolated polynucleotide encoding a Killer Expression protease (Kex2p) or a fragment and/or variant thereof which has at least one Kex2p functional activity, at least one isolated polynucleotide encoding a Protein Disulfide-Isomerase (Pdi1) or a fragment and/or variant thereof which has at least one Pdi1 functional activity and at least one isolated polynucleotide encoding a Endoplasmic Reticulum Oxidoreductin (Ero1) or a fragment and/or variant thereof which has at least one Ero1 functional activity.

In another aspect, the present invention provides genetically modified host cells which expresses or overexpresses at least one gene product of at least one isolated polynucleotide encoding a protein or fragment and/or variant thereof which has at least one functional activity of said protein selected from: Kex2p, Pdi1, or Ero1 when said genetically modified host cell is grown in culture. Another aspect of the present invention provides genetically modified host cells which overexpresses at least two proteins or fragment and/or variant thereof which has at least one functional activity of said at least two proteins selected from: Kex2p, Pdi1, or Ero1 when said genetically modified host cell is grown in culture compared to wild type host cell wherein said wild type host cell is the same species and grown in same culture conditions but does not overexpresses at least two gene products selected from Kex2p, Pdi1, and Ero1. Host cells may be prokaryotic or eukaryotic. Examples of host cells can include, but are not limited to: HeLa, CHO, COS, HEK293, THPI, Yeast, and insect cells. In particular embodiments, the mammalian cell is a hamster, human, or murine cell. In a specific embodiment, the cell is a CHO cell line, an HEK 293 cell line, or a BHK cell line.

Also provided herein are methods of producing a recombinant polypeptide comprising culturing a host cell of the present invention. In another aspect, the present invention provides recombinant polypeptides made by methods of the present invention. Also provided herein are pharmaceutical compositions comprising of recombinant polypeptides made by methods of the present invention. In another aspect of the present invention, methods of treating a patient in need thereof, comprising administering a therapeutically effective amount of a pharmaceutical composition of the present invention, are provided.

BRIEF DESCRIPTION OF THE FIGURES

FIG. 1. Creation of Preliminary Master Cell Bank of Albiglutide producing strain. Steps from KEX2-KanMX Expression cassette PCR product to BXP10KEX2PDIERO1 Production Host are the sequential integrations of expression cassettes to construct Process IV host strain, BXP10_KEX2_PDI_ERO1. After transformation of pCID3610 plasmid, the final production clone was selected and was used in making a Preliminary Master Cell Bank (PCB).

FIG. 2: Southern blot analysis of PDI1 and KEX2 in the host strains. The endogenous KEX2 and PDI1 genes are located in the chromosome XIV and III, respectively, as a single copy (wild type). The target site of integration was shown below the wild type in the chromosome XII. The detecting probes for each gene are shown as solid rectangle.

FIG. 3: Western blot analysis of Pdi1 and Kex2p from the host strains. Samples in the lane, Lanes 1-5: 5 clones of BXP10-KEX2-PDI1 strain; PDI: BXP10 overexpressing Pdi1; KEX2: BXP10 overexpressing Kex2p; and BXP10: host strain as a control. Equivalent amount of proteins were loaded.

FIG. 4. SDS-PAGE of 12 supernatant samples from shaking plate test. Lanes in the gel; L: SeeBlue2 prestained protein ladder (Invitrogen); RS. Reference standard of pCID3610 protein; 1-12: 12 subclones expressing pCID3610.

FIG. 5: Analysis of titer (A) and quality (B) of pCID3610 protein produced in DasGip fermentation run. The supernatant titer yield and 6-AA levels (%) of pCID3610 protein were compared with BXP10-KEX2-PDI1, as a control, which is BXP10 overexpressing Kex2p and Pdi1.

FIG. 6: Growth curves generated from Research Cell Bank Vial cells.

FIG. 7: Growth curves generated from Pre-Master Cell Bank cells.

DETAILED DESCRIPTION OF THE INVENTION

"Host cell(s)" as used herein refers to a cell that has been introduced (e.g., transformed, infected or transfected) or is capable of introduction (e.g., transformation, infection or transfection) by an isolated polynucleotide sequence. Host cells of the present invention may include, but are not limited to bacterial cells, fungal cells, yeast cells, a cell of a microorganism, insect cells and mammalian cells. The host cells of the present invention of yeast and/or filamentous fungal origin may include, but are not limited to, the following families, genie, and species: *Pichia pastoris, Pichia finlandica, Pichia trehalophila, Pichia koclamae, Pichia membranaefaciens, Pichia methanolica, Pichia minuta* (*Ogataea minuta, Pichia lindneri*), *Pichia opuntiae, Pichia thermotolerans, Pichi salictaria, Pichia guercum, Pichia pijperi, Pichia stiptis, Pichia* sp., *Saccharomyces castelii, Saccharomyces cerevisiae, Saccharomyces kluyveri, Saccharomyces* sp., *Schizosaccharomyces pombe, Schizosaccharomyces japonicus, Schizosaccharomyces octosporus, Schizosaccharomyces cryophilus, Schizosaccharomyces* sp., *Hansenula polymorphs, Kluyveromyces* sp., *Kluyveromyces lactis, Candida albicans, Candida* sp., *Aspergillus fumigatus, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens, Yarrowia lipolytica, Arxula adeninivorans, Schwanniomyces occidentalis*, and *Neurospora crassa.*

"Transformed" as known in the art, is the directed modification of an organism's genome or episome via the introduction of external DNA or RNA, or to any other stable introduction of external DNA or RNA.

"Transfected" as known in the art, is the introduction of external DNA or RNA into a microorganism, including but not limited to recombinant DNA or RNA.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:

Algorithm: Needleman and Wunsch, J. Mol Biol. 48: 443-453 (1970) Comparison matrix: BLOSSUM62 from Hentikoff and Hentikoff, Proc. Natl. Acad. Sci. USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to a reference sequence, for example, SEQ ID NO:3, wherein said polynucleotide sequence may be identical to the reference sequence of SEQ ID NO:3 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:3 by the integer defining the percent identity divided by 100 and then subtracting that product from said total number of nucleotides in SEQ ID NO:3, or:

$$n_n \leq x_n - (x_n \cdot y),$$

wherein $n_n$ is the number of nucleotide alterations, $x_n$ is the total number of nucleotides in SEQ ID NO:3, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding a polypeptide may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 50, 60, 70, 80, 85, 90, 95, 97 or 100% identity to a polypeptide reference sequence, such as SEQ ID NO:1, wherein said polypeptide sequence may be identical to the reference sequence or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids by the integer defining the percent identity divided by 100 and then subtracting that product from said total number of amino acids, or:

$$n_a \leq x_a - (x_a \cdot y),$$

wherein $n_a$ is the number of amino acid alterations, $x_a$ is the total number of amino acids in the sequence, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated," including, but not limited to, when such polynucleotide or polypeptide is introduced back into a cell.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered, for example, increased, decreased or eliminated. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein "nucleic acid sequence encoding a functional gene product" refers to any portion of an encoding part of a gene. The nucleic acid sequence encoding a functional gene product may be a portion of an enzyme that is capable of doing at least one activity of the whole enzyme or an entire enzyme.

As used herein "nucleic acid necessary for expression of at least one gene product" refers to a nucleic acid sequence that encodes any portion of a gene and/or is operably linked to a nucleic acid encoding a gene product but does not necessarily comprise encoding sequence. By way of example, a nucleic acid sequence necessary for the expression of at least one gene product includes, but is not limited to, enhancers, promoters, regulatory sequences, start codons, stop codons, polyadenylation sequences, and/or encoding sequences.

As used herein "proteolysis" or "gene product responsible for proteolysis in a cell" refers to any peptide, polypeptide, protein and/or enzyme or portion thereof capable of causing the cleavage of at least one peptide, polypeptide and/or protein. The gene product responsible for proteolysis may be directly responsible for cleavage (ie, a peptidase) or it may be indirectly responsible as part of a peptidase synthesis pathway. Examples of gene products that are responsible for proteolysis in a cell include, but are not limited to, aspartyl proteases, serine proteases, secreted aspartyl proteases, secreted serine proteases, yeast methyltrophic proteases, DPP IV like endopeptidases, metalloendopeptidases, Prb1-like serine proteases, Prb1 serine proteases, and CPY like carboxypeptidases. Also, included in this definition are protease that may be secreted from a cell, but still maintain some or all of it proteolysis activity, such as a secreted serine protease. A secreted protease may be responsible for proteolysis within the cell and/or outside the cell.

As used herein "glycosylation" or "gene product responsible for glycosylation in a cell" refers to any peptide, polypeptide, protein and/or enzyme or portion thereof involved in the addition of at least one saccharide moiety to a polypeptide or elongation of at least one saccharide chain in the cell. The gene product responsible for glycosylation in a cell may be directly responsible for the addition of a saccharide to a polypeptide in a cell, for example, but not limited to mannosyltranferases. Mannosyltransferases may transfer a residue from Dol-P-Man to a serine and/or threonine residue on a peptide, polypeptide and/or protein or may act to transfer a mannose residue from GPD-Man to a saccharide, thus, elongating the saccharide chain. Alternatively, the gene product responsible for glycosylation may be part of a glycosylation pathway and may be indirectly responsible for the addition of polysaccharide to a polypeptide in a cell. Examples of gene products that are responsible for glycosylation in a cell include, but are not limited to mannosyltranferases.

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. The present invention also includes include variants of each of the polypeptides of the invention, that is polypeptides that vary from the reference sequence by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly there are variants in which several, 5-10, 1-5, 1-3, 1-2 or 1 amino acids are substituted, deleted, or added in any combination. Non-naturally occurring variants of polynucleotides and polypeptides may be made by mutagenesis techniques or by direct synthesis. Variants may also include, but are not limited to, polypeptides or fragments thereof having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ϵ-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

As used herein "fragment," when used in reference to a polypeptide, is a polypeptide having an amino acid sequence that is the same as part but not all of the amino acid sequence of the entire naturally occurring polypeptide. As used herein "fragment," when used in reference to a polynucleotide or nucleic acid sequence is a polynucleotide encoding an amino acid sequence that is the same as part but not all of the amino acid sequence of an entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-36 of naturally occurring GLP-1 may also be a variant having amino acid substitutions within its partial sequence. By way of another example "fragment" may refer to any heterologous polypeptide or nucleic acid encoding said polypeptide described herein, including but not limited to Kex2P, Pdi1, and Ero1, wherein said fragment retains at least one functional activity of said wild type polypeptide or enzyme.

As used herein "conjugate" or "conjugated" refers to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone. Recombinant polypeptides expressed in host cells of the present invention may comprise at least one therapeutic polypeptide conjugated to human serum albumin. Other conjugates also include, but are not limited to, at least one therapeutic polypeptides conjugated to transferrin, a single chain variable domain, and/or at least one Fc region of an antibody. Conjugates may or may not comprise a linker.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein "albiglutide" refers to a recombinant fusion protein consisting of 2 copies of a 30-amino acid sequence of modified human glucagon-like peptide 1 (GLP-1, fragment 7-36(A8G)) genetically fused in series to recombinant human serum albumin. The amino acid sequence of albiglutide is shown below as SEQ ID NO:1.

```
                                                      (SEQ ID NO: 1)
HGEGTFTSDVSSYLEGQAAKEFIAWLVKGRHGEGTFTSDVSSYLEGQAAKEFIAWLVKGR  60

DAHKSEVAHRFKDLGEENFKALVLIAFAQYLQQCPFEDHVKLVNEVTEFAKTCVADESAE 120

NCDKSLHTL FGDKLCTVATLRETYGEMADCCAKQEPERNECFLQHKDDNPNLPRLVRPE 180

VDVMCTAFHDNEETFLKKYLYEIARRHPYFYAPELLFFAKRYKAAFTECCQAADKAACLL 240

PKLDELRDEGKASSAKQRLKCASLQKFGERAFKAWAVARLSQRFPKAEFAEVSKLVTDLT 300

KVHTECCHGDLLECADDRADLAKYICENQDSISSKLKECCEKPLLEKSHCIAEVENDEMP 360

ADLPSLAADFVESKDVCKNYAEAKDVFLGMFLYEYARRHPDYSVVLLLRLAKTYETTLEK 420

CCAAADPHECYAKVFDEFKPLVEEPQNLIKQNCELFEQLGEYKFQNALLVRYTKKVPQVS 480

TPTLVEVSRNLGKVGSKCCKHPEAKRMPCAEDYLSVVLNQLCVLHEKTPVSDRVTKCCTE 540

SLVNRRPCFSALEVDETYVPKEFNAETFTFHADICTLSEKERQIKKQTALVELVKHKPKA 600

TKEQLKAVMDDFAAFVEKCCKADDKETCFAEEGKKLVAASQAALGL               674
```

"Recombinant expression system(s)" refers to expression systems or portions thereof or polynucleotides of the invention introduced, transfected or transformed into a host cell or host cell lysate for the production of the polynucleotides and polypeptides of the invention.

As used herein, "albumin fusion protein" comprises at least a fragment or variant of a therapeutic polypeptide and at least a fragment or variant of human serum albumin, which are associated with one another, preferably by genetic fusion.

Polypeptides having GLP-1 activity may comprise at least one fragment and/or variant of human GLP-1. The two naturally occurring fragments of human GLP-1 are represented in SEQ ID NO:2.

```
                                              (SEQ ID NO: 2)
7   8   9   10  11  12  13  14  15  16  17
His-Ala-Glu-Gly-Thr-Phe-Thr-Ser-Asp-Val-Ser-

18  19  20  21  22  23  24  25  26  27  28
Ser-Tyr-Leu-Glu-Gly-Gln-Ala-Ala-Lys-Glu-Phe-

29  30  31  32  33  34  35  36  37
Ile-Ala-Trp-Leu-Val-Lys-Gly-Arg-Xaa
```

wherein: Xaa at position 37 is Gly (hereinafter designated as "GLP-1(7-37)"), or —$NH_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO.: 2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

As used herein "KEX2" refers to a gene encoding the protein referred to as "Killer Expression protease" or "Kex2p" also referred to herein as "kexp." Kex2p is a calcium dependent serine protease involved in proprotein processing. This protease cleaves polypeptides at the carboxyl end of the recognition sequences: Arg-Arg/X and Lys-Arg/X. Other Kex2p activities include, but are not limited to, hydrolase activity, metal ion binding activity, serine-type endopeptidase activity, peptidase activity and serine-type peptidase activity. Pseudonyms for KEX include: Pcsk2, Pcsk4, kpc-1. *Saccharomyces cerevisiae* endopeptidase (KEX2) gene has GenBank ID No. 855483 and encodes NCBI protein sequence Ref Seq NP:014161.1. The KEX2 gene is conserved in fruit fly, *S. cerevisiae, K. lactis, E. gossypii, S. pombe, M. oryzae*, and *N. crassa*. A variant of KEX2 may be a polynucleotide which has at least 85%, 90%, 95%, 96%, 97%, 98%, 99% sequence identity to (KEX2) gene from *Saccharomyces cerevisia* or encodes a protein which has an amino acid sequence with at least 85%, 90%, 95%, 96%, 97%, 98%, 99% sequence identity to Kex2p from *Saccharomyces cerevisiae*. A functional fragment and/or variant of Kex2p would retain at least one function of Kex2p, including but not limited to, the ability to cleave polypeptides at the carboxyl end of the recognition sequences: Arg-Arg/X and Lys-Arg/X. The gene sequence of KEX2 (SEQ ID NO:3) and corresponding amino acid sequence of Kex2p (SEQ ID NO:4) from *S. cerevisiae* is shown below:

```
ORIGIN S. cerevisiae
                                                          (SEQ ID NO: 3)
   1 atgaaagtga ggaaatatat tactttatgc ttttggtggg ccttttcaac atccgctctt

  61 gtatcatcac aacaaattcc attgaaggac catacgtcac gacagtattt tgctgtagaa

 121 agcaatgaaa cattatcccg cttggaggaa atgcatccaa attggaaata tgaacatgat

 181 gttcgagggc taccaaacca ttatgttttt tcaaaagagt tgctaaaatt gggcaaaaga

 241 tcatcattag aagagttaca gggggataac aacgaccaca tattatctgt ccatgattta

 301 ttcccgcgta acgacctatt taagagacta ccggtgcctg ctccaccaat ggactcaagc

 361 ttgttaccgg taaaagaagc tgaggataaa ctcagcataa atgatccgct tttgagagg

 421 cagtggcact tggtcaatcc aagttttcct ggcagtgata taaatgttct tgatctgtgg

 481 tacaataata ttacaggcgc aggggtcgtg gctgccattg ttgatgatgg ccttgactac

 541 gaaaatgaag acttgaagga taatttttgc gctgaaggtt cttgggattt caacgacaat

 601 accaatttac ctaaaccaag attatctgat gactaccatg gtacgagatg tgcaggtgaa

 661 atagctgcca aaaaaggtaa caatttttgc ggtgtcgggg taggttacaa cgctaaaatc

 721 tcaggcataa gaatcttatc cggtgatatc actacggaag atgaagctgc gtccttgatt

 781 tatggtctag acgtaaacga tatatattca tgctcatggg gtcccgctga tgacggaaga

 841 catttacaag gccctagtga cctggtgaaa aaggctttag taaaaggtgt tactgaggga

 901 agagattcca aaggagcgat ttacgttttt gccagtggaa atggtggaac tcgtggtgat

 961 aattgcaatt acgacggcta tactaattcc atatattcta ttactattgg ggctattgat

1021 cacaaagatc tacatcctcc ttattccgaa ggttgttccg ccgtcatggc agtcacgtat

1081 tcttcaggtt caggcgaata tattcattcg agtgatatca acggcagatg cagtaatagc

1141 cacggtggaa cgtctgcggc tgctccatta gctgccggtg tttacacttt gttactagaa

1201 gccaacccaa acctaacttg gagagacgta cagtatttat caatcttgtc tgcggtaggg

1261 ttagaaaaga acgctgacgg agattggaga gatagcgcca tggggaagaa atactctcat

1321 cgctatggct ttggtaaaat cgatgcccat aagttaattg aaatgtccaa gacctgggag

1381 aatgttaacg cacaaacctg gttttacctg ccaacattgt atgtttccca gtccacaaac

1441 tccacggaag agacattaga atccgtcata accatatcag aaaaaagtct tcaagatgct

1501 aacttcaaga gaattgagca cgtcacggta actgtagata ttgatacaga aattagggga

1561 actacgactg tcgatttaat atcaccagcg ggataattt caaaccttgg cgttgtaaga

1621 ccaagagatg tttcatcaga gggattcaaa gactggacat tcatgtctgt agcacattgg
```

-continued

```
1681 ggtgagaacg gcgtaggtga ttggaaaatc aaggttaaga caacagaaaa tggacacagg

1741 attgacttcc acagttggag gctgaagctc tttggggaat ccattgattc atctaaaaca

1801 gaaactttcg tctttggaaa cgataaagag gaggttgaac cagctgctac agaaagtacc

1861 gtatcacaat attctgccag ttcaacttct atttccatca gcgctacttc tacatcttct

1921 atctcaattg gtgtggaaac gtcggccatt ccccaaacga ctactgcgag taccgatcct

1981 gattctgatc caaacactcc taaaaaactt tcctctccta ggcaagccat gcattatttt

2041 ttaacaatat ttttgattgg cgccacattt ttggtgttat acttcatgtt ttttatgaaa

2101 tcaaggagaa ggatcagaag gtcaagagcg gaaacgtatg aattcgatat cattgataca

2161 gactctgagt acgattctac tttggacaat ggaacttccg gaattactga gcccgaagag

2221 gttgaggact tcgattttga tttgtccgat gaagaccatc ttgcaagttt gtcttcatca

2281 gaaaacggtg atgctgaaca tacaattgat agtgtactaa caaacgaaaa tccatttagt

2341 gaccctataa agcaaaagtt cccaaatgac gccaacgcag aatctgcttc caataaatta

2401 caagaattac agcctgatgt tcctccatct tccggacgat cgtga
```

ORIGIN *S. cerevisiae*

(SEQ ID NO: 4)

```
  1 mkvrkyitlc fwwafstsal vssqqiplkd htsrqyfave snetlsrlee mhpnwkyehd

 61 vrglpnhyvf skellklgkr ssleelqgdn ndhilsvhdl fprndlfkrl pvpappmdss

121 llpvkeaedk lsindplfer qwhlvnpsfp gsdinvldlw ynnitgagvv aaivddgldy

181 enedlkdnfc aegswdfndn tnlpkprlsd dyhgtrcage iaakkgnnfc gvgvgynaki

241 sgirilsgdi ttedeaasli ygldvndiys cswgpaddgr hlqgpsdlvk kalvkgvteg

301 rdskgaiyvf asgnggtrgd ncnydgytns iysitigaid hkdlhppyse gcsavmavty

361 ssgsgeyihs sdingrcsns hggtsaaapl aagvytllle anpnltwrdv qylsilsavg

421 leknadgdwr dsamgkkysh rygfgkidah kliemsktwe nvnaqtwfyl ptlyvsqstn

481 steetlesvi tisekslqda nfkriehvtv tvdidteirg tttvdlispa giisnlgvvr

541 prdvssegfk dwtfmsvahw gengvgdwki kvkttenghr idfhswrlkl fgesidsskt

601 etfvfgndke evepaatest vsqysassts isisatstss isigvetsai pqtttastdp

661 dsdpntpkkl ssprqamhyf ltifligatf lvlyfmffmk srrrirrsra etyefdiidt

721 dseydstldn gtsgitepee vedfdfdlsd edhlaslsss engdaehtid svltnenpfs

781 dpikqkfpnd anaesasnkl qelqpdvpps sgrs
```

As used herein, "PDI" or "PDI1" refers to a gene encoding "pdi" or "Pdi1p" also known as "protein disulfide isomerase" which is an enzyme in the endoplasmic reticulum in eukaryotes that catalyzes the formation and breakage of disulfide bonds between cysteine residues within proteins as they fold. (Wilkinson B, Gilbert H F (June 2004). "Protein disulfide isomerase". *Biochimica et Biophysica Acta* 1699 (1-2): 35-44 and Gruber C W, Cemazar M, Heras B, Martin J L, Craik D J (August 2006). "Protein disulfide isomerase: the structure of oxidative folding". *Trends in Biochemical Sciences* 31 (8): 455-64)) and can act as a chaperone protein (Wang, C C and Tsou, C L FASEB J. 1993 December; 7(15):1515-7). Protein disulfide isomerase is a multifunctional protein resident in the endoplasmic reticulum lumen, essential for the formation of disulfide bonds in secretory and cell-surface proteins, unscrambles non-native disulfide bonds; forms a complex with Mnl1p that has exomannosidase activity, processing unfolded protein-bound Man8GlcNAc2 oligosaccharides to Man7GlcNAc2 which promotes degradation in the unfolded protein response. Pdi1 also has oxidative reductase activity. Pdi1p from *S. cerevisiae* is encoded by GenBank ID NO. 850314. A functional fragment and/or variant of pdi may be a polypeptide which has at least 85%, 90%, 95%, 96%, 97%, 98%, 99% sequence identity to the amino acid sequence of NCBI Ref Seq NP_009887 encoded by a polynucleotide having at least 85%, 90%, 95%, 96%, 97%, 98%, 99% sequence identity to GenBank ID No. 850314 and would retain at least one function of Pdi, including but not limited to, isomerase activity. Pdi1 functional activity includes, but is not limited to, catalyzing formation and/or breakage of disulfide bonds, aiding proper folding of misfolded proteins. Pseudonyms for PDI include: PDI1, PDIA2, Pdia3, P4HB, PADI1, Padi2, EUG1, NCU09223, SOAC1F5.02, and AGOS_AFR718W. The PDI1 gene is conserved in human, Rhesus monkey, dog, cow, mouse, rat, chicken, zebrafish, fruit fly, mosquito, *C. elegans, S. cerevisiae, K. lactis, E. gossypii, S. pombe, M. oryzae, N. crassa, A. thaliana*, and rice. (PDI1) can perform. The gene sequence of PDI (SEQ ID NO:5) and corresponding amino acid sequence of Pdi1 (SEQ ID NO:6) from *S. cerevisiae* are shown below:

ORIGIN *S. cerevisiae*

(SEQ ID NO: 5)

```
   1 atgaagtttt ctgctggtgc cgtcctgtca tggtcctccc tgctgctcgc ctcctctgtt
  61 ttcgcccaac aagaggctgt ggcccctgaa gactccgctg tcgttaagtt ggccaccgac
 121 tccttcaatg agtacattca gtcgcacgac ttggtgcttg cggagttttt tgctccatgg
 181 tgtggccact gtaagaacat ggctcctgaa tacgttaaag ccgccgagac tttagttgag
 241 aaaaacatta ccttggccca gatcgactgt actgaaaacc aggatctgtg tatggaacac
 301 aacattccag ggttcccaag cttgaagatt ttcaaaaaca gcgatgttaa caactcgatc
 361 gattacgagg gacctagaac tgccgaggcc attgtccaat tcatgatcaa gcaaagccaa
 421 ccggctgtcg ccgttgttgc tgatctacca gcttaccttg ctaacgagac ttttgtcact
 481 ccagttatcg tccaatccgg taagattgac gccgacttca acgccacctt ttactccatg
 541 gccaacaaac acttcaacga ctacgacttt gtctccgctg aaaacgcaga cgatgatttc
 601 aagctttcta tttacttgcc ctccgccatg gacgagcctg tagtatacaa cggtaagaaa
 661 gccgatatcg ctgacgctga tgtttttgaa aaatggttgc aagtggaagc cttgccctac
 721 tttggtgaaa tcgacggttc cgttttcgcc caatacgtcg aaagcggttt gcctttgggt
 781 tacttattct acaatgacga ggaagaattg gaagaataca agcctctctt taccgagttg
 841 gccaaaaaga acagaggtct aatgaacttt gttagcatcg atgccagaaa attcggcaga
 901 cacgccggca acttgaacat gaaggaacaa ttccctctat ttgccatcca cgacatgact
 961 gaagacttga agtacggttt gcctcaactc tctgaagagg cgtttgacga attgagcgac
1021 aagatcgtgt tggagtctaa ggctattgaa tctttggtta aggacttctt gaaaggtgat
1081 gcctccccaa tcgtgaagtc ccaagagatc ttcgagaacc aagattcctc tgtcttccaa
1141 ttggtcggta agaaccatga cgaaatcgtc aacgacccaa agaaggacgt tcttgttttg
1201 tactatgccc catggtgtgg tcactgtaag agattggccc caacttacca agaactagct
1261 gatacctacg ccaacgccac atccgacgtt ttgattgcta aactagacca cactgaaaac
1321 gatgtcagag gcgtcgtaat tgaaggttac ccaacaatcg tcttataccc aggtggtaag
1381 aagtccgaat ctgttgtgta ccaaggttca agatccttgg actctttatt cgacttcatc
1441 aaggaaaacg gtcacttcga cgtcgacggt aaggccttgt acgaagaagc ccaggaaaaa
1501 gctgctgagg aagccgatgc tgacgctgaa ttggctgacg aagaagatgc cattcacgat
1561 gaattgtaa
```

ORIGIN *S. cerevisiae*

(SEQ ID NO: 6)

```
MKFSAGAVLSWSSLLLASSVFAQQEAVAPEDSAVVKLATDSFNE
YIQSHDLVLAEFFAPWCGHCKNMAPEYVKAAETLVEKNITLAQIDCTENQDLCMEHNI
PGFPSLKIFKNSDVNNSIDYEGPRTAEAIVQFMIKQSQPAVAVVADLPAYLANETFVT
PVIVQSGKIDADFNATFYSMANKHFNDYDFVSAENADDDFKLSIYLPSAMDEPVVYNG
KKADIADADVFEKWLQVEALPYFGEIDGSVFAQYVESGLPLGYLFYNDEEELEEYKPL
FTELAKKNRGLMNFVSIDARKFGRHAGNLNMKEQFPLFAIHDMTEDLKYGLPQLSEEA
FDELSDKIVLESKAIESLVKDFLKGDASPIVKSQEIFENQDSSVFQLVGKNHDEIVND
PKKDVLVLYYAPWCGHCKRLAPTYQELADTYANATSDVLIAKLDHTENDVRGVVIEGY
PTIVLYPGGKKSESVVYQGSRSLDSLFDFIKENGHFDVDGKALYEEAQEKAAEEADAD
AELADEEDAIHDEL
```

PDI is a resident protein in the E.R. lumen of the cells. A body of evidence on the enzyme cellular distribution, its subcellar location and its developmental properties suggests that it plays a role in protein biosynthesis and secretion pathway (Freedman, 1984, *Trends Biochem. Sci.* 9, pp. 438-41) and this is supported by direct cross-linking studies in situ (Roth and Pierce, 1987, *Biochemistry*, 26, pp. 4179-82). The finding that microsomal membranes deficient in PDI show a specific defect in protein disulfide formation (Bulleid and Freedman, 1988, *Nature*, 335, pp. 649-51) implies that the enzyme functions as a catalyst of native disulfide bond formation during the biosynthesis of secretory and cell surface proteins. This role is consistent with what is known of the enzyme's catalytic properties in vitro; it catalyzes thiol: disulfide interchange reactions leading to net protein disulfide formation, breakage or isomerization, and can catalyze protein folding and the formation of native disulfide bonds in a wide variety of reduced, unfolded protein substrates (Freedman et al., 1989, *Biochem. Soc. Symp.*, 55, pp. 167-192). The DNA and amino acid sequence of the enzyme is known for several species (Scherens, B. et al., 1991, *Yeast*, 7, pp. 185-193; Farquhar, R., et al., 1991, *Gene*, 108, pp. 81-89) and there is increasing information on the mechanism of action of the enzyme purified to homogeneity from mammalian liver (Creighton et al., 1980, J. Mol. Biol., 142, pp. 43-62; Freedman et al., 1988, Biochem. Soc. Trans., 16, pp. 96-9; Gilbert, 1989, Biochemistry 28, pp. 7298-7305; Lundstrom and Holmgren, 1990, J. Biol. Chem., 265, pp. 9114-9120; Hawkins and Freedman, 1990, Biochem. J., 275, pp. 335-339). Of the many protein factors currently implicated as mediators of protein folding, assembly and translocation in the cell (Rothman, 1989, Cell 59, pp. 591-601), PDI is unusual in having a well-defined catalytic activity.

PDI is readily isolated from mammalian tissues and the homogeneous enzyme is a homodimer (2×57 kD) with characteristically acidic pI (4.0-4.5) (Hillson et al., 1984, *Methods Enzymol.*, 107, pp. 281-292). The enzyme has also been purified from wheat and from the alga *Chlamydomonas reinhardii* (Kaska et al., 1990 *Biochem. J.* 268, pp. 63-68). The activity has been detected in a wide variety of sources, and in a preliminary report, PDI activity was claimed to be detectable in *S. cerevisiae* (Williams et al., 1968, *FEBS Letts.*, 2, pp. 133-135). Recently, the complete amino acid sequences of a number of PDIs have been reported, largely derived from cloned cDNA sequences; these include the PDIs from rat (Edman et al., 1985, *Nature*, 317, pp. 267-270) bovine (Yamauchi et al., 1987, *Biochem. Biophys. ReS. comm.*, 146, pp. 1485-1492) human (Pihlajaniemi et al., 1987, *EMBO J.*, 6, pp. 643-9), yeast (Scherens, B., et al., supra; Farquhar, R. et al., supra) and chick (Parkkonen et al., 1988, *Biochem. J.*, 256, pp. 1005-1011). The proteins from these vertebrate species show a high degree of sequence conservation throughout and all show several overall features first noted in the rat PDI sequence (Edman et al. 1985 supra).

Sequences corresponding to, or closely related to PDI have been identified in work aimed at analyzing functions other than disulfide bond formation. For example, there is clear-cut evidence that PDI acts as the β-subunits of the tetrameric αβ-enzyme prolyl-4-hydroxylase, which catalyzes a major post-translational modification of nascent or newly-synthesized procollagen polypeptides within the E.R. (Pihlajaniemi et al., 1987, supra; Koivu et al., 1987, *J. Biol. Chem.*, 262, pp. 6447-49)). There is also evidence suggesting that PDI participates in the system for cotranslational N-glycosylation (Geetha-Habib et al., 1988, *Cell*, 4, pp. 63-68) and recently the proposal has been made that the enzyme participates in the complex which transfers triglyceride to nascent secretory lipoproteins (Wetterau at al., 1990, *J. Biol. Chem.*, 265, pp. 9800-7). Thus, PDI may be multifunctional in the co- and post-translational modification of secretory proteins (Freedman, 1989, *Cell*, 57, pp. 1069-72).

Increasing Pdi1 activity in bacterial, yeast, and insect cell expression systems can lead to increased secretion of recombinant proteins containing disulfide bonds. Albiglutide (ALB) the amino acid sequence of which is shown in SEQ ID NO:1 consists of a DPP-4-resistant GLP-1 dimer fused to human albumin. The protein contains 8 disulfide bonds. It is possible that overexpression of Pdi1 can improve the proper folding and secretion of SEQ ID NO:1 in and/or from host cells.

ERO1 is a gene that encodes ER oxidoreductin 1 (Ero1) which is an oxidoreductase enzyme that catalyses the formation and isomerization of protein disulfide bonds in the endoplasmic reticulum (ER) of eukaryotes. (Frand A R, Cuozzo J W, Kaiser C A (2000). "Pathways for protein disulphide bond formation". *Trends Cell Biol.* 10 (5): 203-10 and Frand A R, Kaiser C A (2000). "Two pairs of conserved cysteines are required for the oxidative activity of Ero1p in protein disulfide bond formation in the endoplasmic reticulum". *Mol. Biol. Cell* 11 (9): 2833-43). ERO1 from *S. cerevisiae* has a NCBI Gene ID NO. 854909 and NCBI Protein Ref Seq NP_013576. Pseudonyms for ERO1 include but are not limited to: ERO1L, ERO1LB, Ero1a, Ero1b, ero-1, NCU02074. The ERO1 gene is conserved in human, chimpanzee, Rhesus monkey, dog, cow, mouse, rat, chicken, zebrafish, *C. elegans, S. cerevisiae, K. lactis, E. gossypii, S. pombe, M. oryzae, N. crassa, A. thaliana*, and rice. ERO1 activities include, but are not limited to, flavin adenine dinucleotide binding, oxidoreductase activity, protein disulfide isomerase activity, and thiol oxidase activity. A functional fragment and/or variant of Ero1 would be a polypeptide which maintains at least one functional activity of a wild type Ero1.

"Endoplasmic Reticulum Oxidoreductin" or "ERO" is an oxidoreductase enzyme that catalyses the formation and isomerization of protein disulfide bonds in the endoplasmic reticulum of eukaryote cells. Disulfide bond formation is an oxidative process. After Protein Disulfide-Isomerase (PDI) catalyzes disulfide bond formation in a nascent polypeptide, PDI becomes reduced during the thiol-disulfide exchange reaction. ERO is required for the introduction of oxidizing equivalents to PDI. In *S. cerevisiae*, Endoplasmic Reticulum Oxidoreductin is encoded by ERO1.

The gene sequence of ERO1 (SEQ ID NO:7) and corresponding amino acid sequence of Ero1 (SEQ ID NO:8) from *S. cerevisiae* are shown below:

```
ORIGIN S. cerevisiae
                                                       (SEQ ID NO: 7)
  1 atgagattaa gaaccgccat tgccacactg tgcctcacgg cttttacatc tgcaacttca

 61 aacaatagct acatcgccac cgaccaaaca caaaatgcct ttaatgacac tcacttttgt
```

-continued

```
 121 aaggtcgaca ggaatgatca cgttagtccc agttgtaacg taacattcaa tgaattaaat

 181 gccataaatg aaaacattag agatgatctt tcggcgttat taaaatctga tttcttcaaa

 241 tactttcggc tggatttata caagcaatgt tcattttggg acgccaacga tggtctgtgc

 301 ttaaaccgcg cttgctctgt tgatgtcgta gaggactggg atacactgcc tgagtactgg

 361 cagcctgaga tcttgggtag tttcaataat gatacaatga aggaagcgga tgatagcgat

 421 gacgaatgta agttcttaga tcaactatgt caaaccagta aaaaacctgt agatatcgaa

 481 gacaccatca actactgtga tgtaaatgac tttaacggta aaaacgccgt tctgattgat

 541 ttaacagcaa atccggaacg atttacaggt tatggtggta agcaagctgg tcaaatttgg

 601 tctactatct accaagacaa ctgttttaca attggcgaaa ctggtgaatc attggccaaa

 661 gatgcatttt atagacttgt atccggtttc catgcctcta tcggtactca cttatcaaag

 721 gaatatttga acacgaaaac tggtaaatgg gagcccaatc tggatttgtt tatggcaaga

 781 atcgggaact ttcctgatag agtgacaaac atgtatttca attatgctgt tgtagctaag

 841 gctctctgga aaattcaacc atatttacca gaattttcat tctgtgatct agtcaataaa

 901 gaaatcaaaa acaaaatgga taacgttatt tcccagctgg acacaaaaat ttttaacgaa

 961 gacttagttt ttgccaacga cctaagtttg actttgaagg acgaattcag atctcgcttc

1021 aagaatgtca cgaagattat ggattgtgtg caatgtgata gatgtagatt gtggggcaaa

1081 attcaaacta ccggttacgc aactgccttg aaaattttgt ttgaaatcaa cgacgctgat

1141 gaattcacca aacaacatat tgttggtaag ttaaccaaat atgagttgat tgcactatta

1201 cagactttcg gtagattatc tgaatctatt gaatctgtta acatgttcga aaaaatgtac

1261 gggaaaaggt taaacggttc tgaaaacagg ttaagctcat tcttccaaaa taacttcttc

1321 aacattttga aggaggcagg caaatcgatt cgttacacca tagagaacat caattccact

1381 aaagaaggaa agaaaaagac taacaattct caatcacatg tatttgatga tttaaaaatg

1441 cccaaagcag aaatagttcc aaggccctct aacggtacag taaataaatg gaagaaagct

1501 tggaatactg aagttaacaa cgttttagaa gcattcagat ttatttatag aagctatttg

1561 gatttaccca ggaacatctg ggaattatct ttgatgaagg tatacaaatt ttggaataaa

1621 ttcatcggtg ttgctgatta cgttagtgag gagacacgag agcctatttc ctataagcta

1681 gatatacaat aa
```

ORIGIN *S. cerevisiae*

(SEQ ID NO: 8)

```
MRLRTAIATLCLTAFTSATSNNSYIATDQTQNAFNDTHFCKVDR

NDHVSPSCNVTFNELNAINENIRDDLSALLKSDFFKYFRLDLYKQCSFWDANDGLCLN

RACSVDVVEDWDTLPEYWQPEILGSFNNDTMKEADDSDDECKFLDQLCQTSKKPVDIE

DTINYCDVNDFNGKNAVLIDLTANPERFTGYGGKQAGQIWSTIYQDNCFTIGETGESL

AKDAFYRLVSGFHASIGTHLSKEYLNTKTGKWEPNLDLFMARIGNFPDRVTNMYFNYA

VVAKALWKIQPYLPEFSFCDLVNKEIKNKMDNVISQLDTKIFNEDLVFANDLSLTLKD

EFRSRFKNVTKIMDCVQCDRCRLWGKIQTTGYATALKILFEINDADEFTKQHIVGKLT

KYELIALLQTFGRLSESIESVNMFEKMYGKRLNGSENRLSSFFQNNFFNILKEAGKSI

RYTIENINSTKEGKKKTNNSQSHVFDDLKMPKAEIVPRPSNGTVNKWKKAWNTEVNNV

LEAFRFIYRSYLDLPRNIWELSLMKVYKFWNKFIGVADYVSEETREPISYKLDIQ"
```

"Microorganism(s)" means a (i) prokaryote, including but not limited to, a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (ii) an archaeon, including but not limited to *Archaebacter*, and (iii) a unicellular or filamentous eukaryote, including but not limited to, a protozoan, a fungus, a member of the genus *Saccharomyces, Kluveromyces*, or *Candida*, and a member of the species *Saccharomyces ceriviseae, Kluveromyces lactis*, or *Candida albicans.*

"Bacteria(um)(l)" means a (i) prokaryote, including but not limited to, a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, and (ii) an archaeon, including but not limited to *Archaebacter.*

As used herein, "heterologous nucleic acid sequence" refers to a nucleic acid sequence which is inserted, transformed, or transfected into a host cell or microorganism of interest. A heterologous nucleic acid sequence may be a coding sequence for all or part of a polypeptide and/or it may comprise non-coding regulatory elements such as a promoter, enhancer, ribosome binding element or polyadenylation region. A heterologous nucleic acid sequence may be a nucleic acid sequence which not naturally found in the host cell, such as a nucleic acid sequence that encodes a polypeptide from a different organism, genus or species than the host cell. Alternatively, a heterologous nucleic acid sequence may be native to a host cell's genome but is inserted, transformed or transfected into the host cell to increase the function of native nucleic acid sequence or expression of polypeptide encoded by said nucleic acid sequence. For example, wild type *S. cerevisiae* may contain nucleic acid sequences which encode wild type Kex2p, but a heterologous nucleic acid encoding wild type Kex2p may be transformed into said *S. cerevisiae* to increase Kex2p production by said host cell. Similarly, wild type *S. cerevisiae* may contain nucleic acid sequences which encode wild type Kex2p, but a heterologous nucleic acid encoding Kex2p from a different organism may be inserted into said *S. cerevisiae* to increase Kex2p production by said host cell. Also contemplated by the present invention are host cells that contain heterologous nucleic acids sequences which are variants and/or fragments of wild nucleic acids from the same species of host cell.

As used herein, "recombinant polypeptide(s)" and grammatical variations thereof refers to a polypeptide not naturally synthesized by a transformed host cell or microorganism of interest and introduced into the host cell or microorganism by recombinant DNA. For example, *S. cerevisiae* may act as a host cell for the expression of human serum albumin, which does not occur in non-transformed or non-transfected *S. cerevisiae*. Recombinant polypeptides may include polypeptides that have been modified to facilitate isolation.

As used herein "affinity tag" refers to any moiety associated with a molecule that may give said molecule a selective affinity for another substance or molecule. For instance, an affinity tag may be used to facilitate purification of a molecule by providing the molecule with a selective affinity for a column's packing material. A non-limiting example of an affinity tag is a his-tag.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein "harvesting" cells refers to collection of cells from cell culture. Cells may be concentrated during harvest to separate them from culture broth, for instance by centrifugation or filtration. Harvesting cells may further comprise the step of lysing the cells to obtain intracellular material, such as, but not limited to polypeptides and polynucleotides. It should be understood by the skilled artisan that certain cellular material, including but not limited to, heterologously expressed polypeptide, may be released from cells during culture. Thus, a product (e.g., a recombinantly expressed polypeptide) of interest may remain in culture broth after cells are harvested.

Also, provided are methods wherein the recombinant DNA construct encodes a selectable marker. Such a selectable marker provides for either positive or negative selection. Methods are also provided comprising expressing said selectable marker and comparing the amount of selectable marker produced by at least one first transformed cell of the selecting step with the amount of selectable marker produced by at least one second transformed cell of the selecting step wherein the first and second transformed cell produce the same selectable marker. As is understood in the art, selectable markers include, but are not limited to, dihydrofolate reductase (dhfr), β-galactosidase, fluorescent protein, secreted form of human placental alkaline phosphatase, beta-glucuronidase, yeast selectable markers LEU2 and URA3, apoptosis resistant genes, and antisense oligonucleotides, as well as antibiotic resistance genes conferring the ability to grow in the presence of antibiotics including, neomycin (neo), kanamycin, geneticin, hygromycin B, puromycin, zeocin, blasticidin, nourseothricin, bialaphos, phleomycin, and ampicillin. As is also understood in the art, cells can be sorted by a variety of means, including but not limited to, visual inspection or a cell sorter such as a BD FACS Aria, which can detect expression of a selectable marker.

The term "wild type" as is understood in the art refers to a host cell or a polypeptide or polynucleotide sequence that occurs in a native population without genetic modification. For example, a "wild type host cell" refers to an unmodified strain of a host cell prior to any genetic modification being made or occurring in the genome of the host cell.

As used herein, "titer" or "titer yield" refers to the concentration of a product (e.g., recombinantly expressed polypeptide) in solution (e.g., culture broth or cell-lysis mixture or buffer) and it usually expressed as mg/L or g/L. An increase in titer yield may refer to an absolute or relative increase in the concentration of a product produced under two defined set of conditions.

"Incretin hormone" as used herein means any hormone that potentiates insulin secretion or otherwise raises the level or insulin. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. *Biodrugs* 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level or insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent while the stimulation of insulin production may indirectly reduce plasma glucose levels in a mammal.

An "incretin mimetic" as used herein is a compound capable of potentiating insulin secretion or otherwise raise the level or insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "domain antibodies". As used herein $V_H$ includes camelid $V_{HH}$ domains.

The phrase "single variable domain" refers to an antigen binding protein variable domain (for example, $V_H$, $V_{HH}$, $V_L$) that specifically binds an antigen or epitope independently of a different variable region or domain.

The term "antigen binding protein" as used herein refers to antibodies, antibody fragments and other protein constructs, such as domains, but not limited to, variable domains and domain antibodies, which are capable of binding to an antigen.

As used herein, "reduced amount" and grammatical variations thereof of an enzyme or fragment thereof or enzyme activity compared in a genetically modified host cell refers to a genetically modified host cell which produces less of at least one enzyme or shows less of at least one kind of enzyme activity when compared with a non-genetically modified host cell. Typically, the comparison in enzyme activity produced by a genetically modified host cell is with the wild type strain of the same species before genetic modification. However, the comparison can also be between genetically modified host and a wild type host from the genus but different species or strain or with another genetically modified strain. A reduction in at least one enzyme or enzyme activity also includes a complete abrogation of at least one enzyme or enzyme activity in which none of at least one enzyme is produced in a genetically modified host cell and/or none of at least one enzyme is functional or shows activity. Also included within this definition is a reduced amount of at least one enzyme activity. That is, enzymes which have more then one activity may maintain the amount of a first activity while a second activity of the same enzyme is reduced.

As used herein, "increased amount" and grammatical variations thereof of an enzyme or fragment thereof or enzyme activity in a genetically modified host cell refers to a genetically a genetically modified host cell which produces more of at least one enzyme or shows more of at least one kind of enzyme activity when compared with a non-genetically modified host cell. Typically, the comparison in enzyme activity produced by a genetically modified host cell is with the wild type strain of the same species before genetic modification. However, the comparison can also be between genetically modified host and a wild type host from the genus but different species or strain or with another genetically modified strain. Also included within this definition is an increased amount of at least one enzyme activity. That is, enzymes which have more then one activity may maintain the amount of a first activity while a second activity of the same enzyme is increased. Additionally, this term includes increases in enzyme activity apart from the amount of enzyme produced by a host cell. For instance, a genetically modified host cell may produced the same or similar amount of an enzyme or fragment and/or variant thereof that is produced by a wild type host cell as measured by mass or quantity but there may be a measurable increase in the amount of at least one functional activity of said enzyme compared with wild type.

As herein used, the terms "stringent conditions" and a "stringent hybridization conditions" mean hybridization will occur only if there is at least 70% and at least 80%, but at least 95% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

As used herein "genetic modification" or "genetically modified" refers to any suppression, substitution, deletion and/or insertion of one or more bases or of a fragment of a cell DNA sequence(s). Such genetic modification may be obtained in vitro (directly on isolated DNA) or in situ, for example by genetic engineering techniques or by exposing the cells to a mutagenic agent. Mutagenic agents include, for example, physical agents such as energetic rays (X-rays, γ-rays, UV, etc.) or chemical agents capable of reacting with different functional groups of DNA, such as alkylating agents (EMS, NQO, etc.) bialkylating agents, intercalating agents, etc. Genetic modifications may also be obtained by genetic disruption for example according to the method disclosed by Rothstein et al. (*Meth. Enzymol.* 194:281-301 (1991)). According to this method, part or all of a gene is replaced through homologous recombination by an in vitro modified version. Genetic modifications can also be obtained by any mutation insertion on DNA sequences, such as transposons, phages, etc. Also, as used herein "genetically modified" can refer to a gene encoding a polypeptide or a polypeptide having at least one deletion, substitution or suppression of a nucleic acid or amino acid, respectively. For example, a polypeptide in which at least one amino acid is substituted from the wild type form would be considered genetically modified.

Genetic modification may be reversed or attenuated by cellular mechanism. Alternatively, mutations can be non-reverting and or non-leaky. "Leaky mutations" include mutations that result in a partial rather than a complete inactivation of wild type function.

The genetic modifications carried by the host cells of the invention may be located in a coding region of the DNA sequence of the cell and/or in a region affecting the expression of a gene. Modifications of the invention will generally, therefore, affect gene product or regulation or promotion of gene product of proteins and/or enzymes involved in proteolysis and/or glycosylation. The reduced capacity of the cells of the invention to proteolytically cleave and/or glycosylate a heterologously expressed polypeptide may be due to structural and/or conformational changes, from the production of one or more enzymes having altered biological properties, from the absence of production of said one or more enzymes or from the production of one or more enzymes at low levels.

The genetic modifications of the invention also affect gene product or regulation or promotion of gene product of proteins and/or enzymes involved in any of the functional activities of Kex2p. Pdi1, and ero1 described herein. The increased capacity of the cells of the invention to properly fold and secrete recombinantly expressed polypeptides may be due to enzymes involved in these processes having altered biological properties or being produced at high levels.

In one aspect of the present invention, genetically modified host cells are provided comprising at least one isolated polynucleotide encoding a Killer Expression (KEX) protease (Kex2p) or a fragment and/or variant thereof which has at least one Kex2p protease functional activity and at least one isolated polynucleotide encoding a Protein Disulfide-Isomerase (PDI) or a fragment and/or variant thereof which has at least one Pdi1 functional activity. The genetically modified host cell of the present invention include genetically modified host cells comprising at least one isolated polynucleotide encoding Endoplasmic Reticulum Oxidoreductin (ero1) or a fragment and/or variant thereof which has at least one ERO functional activity.

Genetically modified host cells of the present invention also include genetically modified host cells which express or overexpresses at least one gene product of at least one isolated polynucleotide encoding a protein and/or variant thereof which has at least one functional activity of said protein selected from: Kex2p, Pdi1, or Ero1 when said genetically modified host cell is grown in culture, compared to second host cell wherein said second host cell does not express or overexpress at least one gene product selected from KEX, PDI, and ERO. Also included in the present invention are genetically modified host cells which overexpresses at least two proteins or fragment and/or variant thereof which has at least one functional activity of said protein selected from: Kex2p, Pdi1, or Ero1 when said genetically modified host cell is grown in culture compared to a second host cell wherein said second host cell is the same species and grown in the same culture conditions but does not overexpress at least two gene product selected from KEX, PDI and ERO. In some instances, the second host cell may have genetic modification, but does not have genetic modifications that allow it to express or overexpress at least one gene product of at least one isolated polynucleotide encoding a protein and/or variant thereof which has at least one functional activity of said protein selected from: Kex2p, Pdi1, or Ero1. In some instances, the second host cell may be a wild type cell (ie, no genetic modifications) of the same species as the modified host cell. In some instances, the second host may contain all of the same genetic modifications as the genetically modified host cell except for comprising a nucleic acid encoding a protein and/or variant thereof which has at least one functional activity of said protein selected from: Kex2p, Pdi1, or Ero1. Also contemplated within this invention are host cells which are genetically modified to increase expression of endogenous polypeptides, including, but not limited to: Kex2p, Pdi1, and Ero1 from genes already contained in the host cell.

In another aspect of the present invention, genetically modified host cells are provided which further comprises at least one of the following genetic modifications: pep4 protease knockout, lower ubc4 and/or ubc5 activity compared with wild type host cell, yps1 knockout, hsp150 knockout, and pmt1 knockout. These genetic modifications have been found to increase recombinant human serum albumin secretion capabilities and decrease unwanted posttranslational modifications.

Yeast strains used in the production of albumin fusion proteins include but are not limited to D88, DXY1 and BXP10. D88 [leu2-3, leu2-122, can1, pra1, ubc4] is a derivative of parent strain AH22his.sup.+ (also known as DB1; see, e.g., Sleep et al. Biotechnology 8:42-46 (1990)). The strain contains a leu2 mutation which allows for auxotropic selection of 2 micron-based plasmids that contain the LEU2 gene. D88 also exhibits a derepression of PRB1 in glucose excess. The PRB1 promoter is normally controlled by two checkpoints that monitor glucose levels and growth stage. The promoter is activated in wild type yeast upon glucose depletion and entry into stationary phase. Strain D88 exhibits the repression by glucose but maintains the induction upon entry into stationary phase. The PRA1 gene encodes a yeast vacuolar protease, YscA endoprotease A, that is localized in the ER. The UBC4 gene is in the ubiquitination pathway and is involved in targeting short lived and abnormal proteins for ubiquitin dependant degradation. Isolation of this ubc4 mutation was found to increase the copy number of an expression plasmid in the cell and cause an increased level of expression of a desired protein expressed from the plasmid (see, e.g., International Publication No. WO99/00504, hereby incorporated in its entirety by reference herein).

DXY1, a derivative of D88, has the following genotype: [leu2-3, leu2-122, can1, pra1, ubc4, ura3:yap3]. In addition to the mutations isolated in D88, this strain also has a knockout of the YAP3 protease. This protease causes cleavage of mostly di-basic residues (RR, RK, KR, KK) but can also promote cleavage at single basic residues in proteins. Isolation of this yap3 mutation resulted in higher levels of full length HSA production (see, e.g., U.S. Pat. No. 5,965,386 and Kerry-Williams et al., Yeast 14:161-169 (1998), hereby incorporated in their entireties by reference herein).

BXP10 has the following genotype: leu2-3, leu2-122, can1, pra1, ubc4, ura3, yap3::URA3, lys2, hsp150::LYS2, pmt1::URA3. In addition to the mutations isolated in DXY1, this strain also has a knockout of the PMT1 gene and the HSP150 gene. The PMT1 gene is a member of the evolutionarily conserved family of dolichyl-phosphate-D-mannose protein O-mannosyltransferases (Pmts). The transmembrane topology of Pmt1p suggests that it is an integral membrane protein of the endoplasmic reticulum with a role in O-linked glycosylation. This mutation serves to reduce/eliminate O-linked glycosylation of HSA fusions (see, e.g., International Publication No. WO00/44772, hereby incorporated in its entirety by reference herein). Studies revealed that the Hsp150 protein is inefficiently separated from rHA by ion exchange chromatography. The mutation in the HSP150 gene removes a potential contaminant that has proven difficult to remove by standard purification techniques. See, e.g., U.S. Pat. No. 5,783,423, hereby incorporated in its entirety by reference herein.

Genetically modified host cells of the present invention include, but are not limited to fungal cells, yeast cells, and mammalian cells. Genetically modified host cells of the present invention include, but are not limited to: *Saccharomyces, Kluyveromyces, Candida, Pichia, Schizosaccharomyces, Hansenula, Kloeckera, Schwanniomyces*, and *Yarrowia*. Genetically modified host cells of the present invention also include, but are not limited to, *S. cerevisiae.*

The genetically modified host cells of the present invention may further comprise at least one polynucleotide encoding a recombinant polypeptide. Polynucleotide capable of expressing at least one heterologous polypeptide include, but are not limited to, vectors, DNA transformed into the genome of the host cell, virus or part of a virus, and/or plasmids. Polynucleotide capable of expressing a heterologous polypeptide may be transformed into the genome of the host cell and/or may be part of an expression vector and/or episomal expression system.

In some aspects of the present invention, the nucleic acid encoding a recombinant polypeptide is contained in a plasmid. In other aspects, the nucleic acid encoding a recombinant polypeptide is transformed into the genome of host cell of the present invention.

As is understood in the art, DNA may be transformed into a host cell by several different methods. In yeast, any convenient method of DNA transfer may be used, such as electroporation, the lithium chloride method, the lithium acetate method, or the spheroplast method. To produce a stable strain suitable for high-density fermentation, it is desirable to integrate the DNA into the host chromosome. Integration occurs via homologous recombination, using techniques known in the art. For example, DNA capable of expressing at least one heterologous protein can be provided with flanking sequences homologous to sequences of the host organism. In this manner, integration occurs at a defined site in the host genome, without disruption of desirable or essential genes. Additionally and alternatively, DNA capable of expressing at least one heterologous protein is integrated into the site of an undesired gene in a host chromosome, effecting the disruption or deletion of the gene or expression of that gene product.

Increased expression, or overexpression, of a gene product may be achieved by integrating extra copies of DNA capable of expressing the gene product into the host chromosome. Additionally and alternatively, DNA encoding the gene product may be operably linked to a strong promoter, and the entire expression cassette may be integrated into the host chromosome at a defined site. For example, integration of DNA encoding Kex2p, Pdi1, or Ero1 operably linked to a strong promoter (e.g. PGK1 promoter) into the site of NTS2-2 allows overexpression of the respective gene product. In other embodiments, DNA may be introduced into the host via a chromosome, plasmid, retroviral vector, or random integration into the host genome.

Genetically modified host cells of the present invention include genetically modified host cells wherein at least one isolated polynucleotide encoding kex protease or a fragment and/or variant thereof which has at least one Kex2p functional activity is operably linked to at least one promoter selected from the group of: TEF1, PRB1 ADH1, ADH2, PYK1, PGK1, ENO, GAL1.10.7, GALS, MET25, CUP1, PHO5, tetO-CYC1, CaMV, HXT6, HXT7, and ARE. Suitably the promoter is PGK1. Genetically modified host cells of the present invention also include genetically modified host cells wherein at least one isolated polynucleotide encoding PDI or a fragment and/or variant thereof which has at least one Pdi1 functional activity is operably linked to at least one promoter selected from the group of: TEF1, PRB1 ADH1, ADH2, PYK1, PGK1, ENO, GAL1.10.7, GALS, MET25, CUP1, PHO5, tetO-CYC1, CaMV, HXT6, HXT7, and ARE. Suitably the promoter is PGK1. Additionally, genetically modified host cells of the present invention includes genetically modified host cells wherein at least one isolated polynucleotide encoding ERO or a fragment and/or variant thereof which has at least one ERO functional activity is operably linked to at least one promoter selected from the group of: TEF1, PRB1 ADH1, ADH2, PYK1, PGK1, ENO, GAL1.10.7, GALS, MET25, CUP1, PHO5, tetO-CYC1, CaMV, HXT6, HXT7, and ARE. Suitably the promoter is PGK1.

In another aspect, recombinant polypeptide expressed in genetically modified host cells of the present invention has at least one disulfide bond. In some aspects, the recombinant polypeptide is an albumin fusion protein. In some aspects, the recombinant polypeptide comprises at least one therapeutic polypeptide having GLP-1 activity conjugated to albumin.

In some aspects, at least one fragment and variant of GLP-1 comprises GLP-1(7-36(A8G)) and is genetically fused to human serum albumin. In a further embodiment, polypeptides of the invention comprise one, two, three, four, five, or more tandemly oriented molecules of GLP-1 and/or fragments and/or variants thereof fused to the N- or C-terminus of human serum albumin or variant thereof. Other embodiments have such A8G polypeptides fused to the N- or C-terminus of albumin or variant thereof. An example of two tandemly oriented GLP-1(7-36)(A8G) fragments and/or variants fused to the N-terminus of human serum albumin comprises SEQ ID NO:1, which is presented in FIG. 3. In another aspect, at least one fragment and variant of GLP-1 comprises at least two GLP-1(7-36(A8G)) tandemly and genetically fused to the human serum albumin. At least two GLP-1(7-36(A8G)) may be genetically fused at the N-terminus of the human serum albumin. At least one polypeptide having GLP-1 activity may comprise SEQ ID NO: 1.

Variants of GLP-1(7-37) may be denoted for example as Glu$^{22}$-GLP-1(7-37)OH which designates a GLP-1 variant in which the glycine normally found at position 22 of GLP-1 (7-37)OH has been replaced with glutamic acid; Val$^{8}$-Glu$^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to,

| | | |
|---|---|---|
| Val$^{8}$-GLP-1(7-37)OH | Gly$^{8}$-GLP-1(7-37)OH | Glu$^{22}$-GLP-1(7-37)O—H |
| Asp$^{22}$-GLP-1(7-37)OH | Arg$^{22}$-GLP-1(7-37)OH | Lys$^{22}$-GLP-1(7-37)OH |
| Cys$^{22}$-GLP-1(7-37)OH | Val$^{8}$-Glu$^{22}$-GLP-1(7-37)OH | Val$^{8}$-Asp$^{22}$-GLP-1(7-37)OH |
| Val$^{8}$-Arg$^{22}$-GLP-1(7-37)OH | Val$^{8}$-Lys$^{22}$-GLP-1(7-37)OH | Val$^{8}$-Cys$^{22}$-GLP-1(7-37)OH |
| Gly$^{8}$-Glu$^{22}$-GLP-1(7-37)OH | Gly$^{8}$-Asp$^{22}$-GLP-1(7-37)OH | Gly$^{8}$-Arg$^{22}$-GLP-1(7-37)OH |
| Gly$^{8}$-Lys$^{22}$-GLP-1(7-37)OH | Gly$^{8}$-Cys$^{22}$-GLP-1(7-37)OH | Glu$^{22}$-GLP-1(7-36)OH |
| Asp$^{22}$-GLP-1(7-36)OH | Arg$^{22}$-GLP-1(7-36)OH | Lys$^{22}$-GLP-1(7-36)OH |
| Cys$^{22}$-GLP-1(7-36)OH | Val$^{8}$-Glu$^{22}$-GLP-1(7-36)OH | Val$^{8}$-Asp$^{22}$-GLP-1(7-36)OH |
| Val$^{8}$-Arg$^{22}$-GLP-1(7-36)OH | Val$^{8}$-Lys$^{22}$-GLP-1(7-36)OH | Val$^{8}$-Cys$^{22}$-GLP-1(7-36)OH |
| Gly$^{8}$-Glu$^{22}$-GLP-1(7-36)OH | Gly$^{8}$-Asp$^{22}$-GLP-1(7-36)OH | Gly$^{8}$-Arg$^{22}$-GLP-1(7-36)OH |
| Gly$^{8}$-Lys$^{22}$-GLP-1(7-36)OH | Gly$^{8}$-Cys$^{22}$-GLP-1(7-36)OH | Lys$^{23}$-GLP-1(7-37)OH |
| Val$^{8}$-Lys$^{23}$-GLP-1(7-37)OH | Gly$^{8}$-Lys$^{23}$-GLP-1(7-37)OH | His$^{24}$-GLP-1(7-37)OH |
| Val$^{8}$-His$^{24}$-GLP-1(7-37)OH | Gly$^{8}$-His$^{24}$-GLP-1(7-37)OH | Lys$^{24}$-GLP-1(7-37)OH |
| Val$^{8}$-Lys$^{24}$-GLP-1(7-37)OH | Gly$^{8}$-Lys$^{23}$-GLP-1(7-37)OH | Glu$^{30}$-GLP-1(7-37)OH |
| Val$^{8}$-Glu$^{30}$-GLP-1(7-37)OH | Gly$^{8}$-Glu$^{30}$-GLP-1(7-37)OH | Asp$^{30}$-GLP-1(7-37)OH |
| Val$^{8}$-Asp$^{30}$-GLP-1(7-37)OH | Gly$^{8}$-Asp$^{30}$-GLP-1(7-37)OH | Gln$^{30}$-GLP-1(7-37)OH |
| Val$^{8}$-Gln$^{30}$-GLP-1(7-37)OH | Gly$^{8}$-Gln$^{30}$-GLP-1(7-37)OH | Tyr$^{30}$-GLP-1(7-37)OH |
| Val$^{8}$-Tyr$^{30}$-GLP-1(7-37)OH | Gly$^{8}$-Tyr$^{30}$-GLP-1(7-37)OH | Ser$^{30}$-GLP-1(7-37)OH |
| Val$^{8}$-Ser$^{30}$-GLP-1(7-37)OH | Gly$^{8}$-Ser$^{30}$-GLP-1(7-37)OH | His$^{30}$-GLP-1(7-37)OH |
| Val$^{8}$-His$^{30}$-GLP-1(7-37)OH | Gly$^{8}$-His$^{30}$-GLP-1(7-37)OH | Glu$^{34}$-GLP-1(7-37)OH |
| Val$^{8}$-Glu$^{34}$-GLP-1(7-37)OH | Gly$^{8}$-Glu$^{34}$-GLP-1(7-37)OH | Ala$^{34}$-GLP-1(7-37)OH |
| Val$^{8}$-Ala$^{34}$-GLP-1(7-37)OH | Gly$^{8}$-Ala$^{34}$-GLP-1(7-37)OH | Gly$^{34}$-GLP-1(7-37)OH |
| Val$^{8}$-Gly$^{34}$-GLP-1(7-37)OH | Gly$^{8}$-Gly$^{34}$-GLP-1(7-37)OH | Ala$^{35}$-GLP-1(7-37)OH |
| Val$^{8}$-Ala$^{35}$-GLP-1(7-37)OH | Gly$^{8}$-Ala$^{35}$-GLP-1(7-37)OH | Lys$^{35}$-GLP-1(7-37)OH |
| Val$^{8}$-Lys$^{35}$-GLP-1(7-37)OH | Gly$^{8}$-Lys$^{35}$-GLP-1(7-37)OH | His$^{35}$-GLP-1(7-37)OH |
| Val$^{8}$-His$^{35}$-GLP-1(7-37)OH | Gly$^{8}$-His$^{35}$-GLP-1(7-37)OH | Pro$^{35}$-GLP-1(7-37)OH |
| Val$^{8}$-Pro$^{35}$-GLP-1(7-37)OH | Gly$^{8}$-Pro$^{35}$-GLP-1(7-37)OH | Glu$^{35}$-GLP-1(7-37)OH |
| Gly$^{8}$-Glu$^{35}$-GLP-1(7-37)OH | Val$^{8}$-Ala$^{27}$-GLP-1(7-37)OH | Val$^{8}$-His$^{37}$-GLP-1(7-37)OH |
| Val$^{8}$-Glu$^{22}$-Lys$^{23}$-GLP-1(7-37)OH | Val$^{8}$-Glu$^{22}$-Glu$^{23}$-GLP-1(7-37)OH | Val$^{8}$-Glu$^{22}$-Ala$^{27}$-GLP-1(7-37)OH |
| Val$^{8}$-Gly$^{34}$-Lys$^{35}$-GLP-1(7-37)OH | Val$^{8}$-His$^{37}$-GLP-1-(7-37)OH | Gly$^{8}$-His$^{37}$-GLP-1(7-37)OH |
| Val$^{8}$-Glu$^{22}$-Ala$^{27}$-GLP-1(7-37)OH | Gly$^{8}$-Glu$^{22}$-Ala$^{27}$-GLP-1(7-37)OH | Val$^{8}$-Lys$^{22}$-Glu$^{23}$-GLP-1(7-37)OH |
| Gly$^{8}$-Lys$^{22}$-Glu$^{23}$-GLP-1(7-37)OH. | Val$^{8}$-Glu$^{35}$-GLP-1(7-37)OH | |

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ϵ-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of said fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

In another aspect, the at least one polypeptide having GLP-1 activity comprises at least one fragment and/or variant of human GLP-1 fused with human serum albumin. In another aspect, at least one fragment and variant of GLP-1 comprises GLP-1(7-36(A8G)). The at least one fragment and variant of GLP-1 is genetically fused to human serum albumin. In another aspect, the recombinant polypeptide of the present invention comprises at least two GLP-1(7-36 (A8G)) tandemly and genetically fused to the human serum albumin. The two GLP-1(7-36(A8G)) are genetically fused at the N-terminus of the human serum albumin. In some instances, the recombinant polypeptide comprises SEQ ID NO:1.

In one embodiment of the present invention, the recombinant polypeptide comprises a polypeptide having 99% sequence identity to the polypeptide set forth in SEQ ID NO:1 or a polypeptide having an amino acid sequence of SEQ ID NO:1 which is truncated at the C-terminus and/or at the N-terminus. In one aspect, the recombinant polypeptide has GLP-1 activity. In one aspect the polypeptide is truncated at the N-terminus by 1, 2, 3, 4, 5, 6, 7, 8, 9, 10 amino acids compared to SEQ ID NO:1 or a polypeptide having 99% sequence identity to SEQ ID NO: 1 over the entire sequence. In one aspect the recombinant polypeptide is truncated at the C-terminus by 1, 2, 3, 4, 5, 6, 7, 8, 9, 10 amino acids compared to SEQ ID NO:1 or a polypeptide having 99% sequence identity to SEQ ID NO: 1 over the entire sequence.

In yet another embodiment, at least one recombinant polypeptide expressed in the host cells of the invention comprises one or more of the following: at least one antigen binding protein, at least one single variable domain, and/or at least one domain antibody. Polypeptides comprising at least one antigen binding domain may also comprise at least one polypeptide and/or peptide receptor agonist and/or antagonist. In some instances, the polypeptide agonist may be a GLP-1 receptor agonist. As is understood in the art, more than one recombinant polypeptide may be expressed in the same cell. By way of example, a recombinant polypeptide having GLP-1 activity can be expressed in the same cell as an antigen binding protein. The polypeptide having GLP-1 activity may be expressed from the same polynucleotide as the antigen binding protein, operably linked to the nucleic acid sequenced necessary for expression. Alternatively, and by way of example, a polypeptide having GLP-1 activity may be expressed independently of a second recombinant polypeptide such as an antigen binding protein, either from the same episome DNA or genome but operably linked to different polynucleotide sequences necessary for expression or from DNA sequences located on separate vectors.

Also provided are genetically modified host cells comprising at least one isolated polypeptide encoding a Killer Expression (KEX) protease (Kex2p) or a fragment and/or variant thereof which has at least one Kex2p functional activity, at least one isolated polypeptide encoding a Protein Disulfide Isomerase (Pdi1) or a fragment and/or variant thereof which has at least one PDI functional activity and at least one heterologous nucleic acid sequence encoding a Endoplasmic Reticulum Oxidoreductin (Ero1) or a fragment and/or variant thereof which has at least one ERO functional activity. The genetically modified host cell of the present invention comprises at least one nucleic acid encoding a recombinant polypeptide. In another aspect of the present invention, the genetically modified host cell increases the expression of said recombinant polypeptide when grown in culture compared with a host cell of the same species and genetic modifications but which does not comprise at least one isolated polynucleotide sequence encoding a Killer Expression (KEX) protease Kex2p or a fragment and/or variant thereof which has at least one KEX functional activity, at least one isolated polynucleotide encoding a Protein Disulfide-Isomerase (Pdi1) or a fragment and/or variant thereof which has at least one Pdi1 functional activity and at least one isolated polynucleotide encoding a Endoplasmic Reticulum Oxidoreductin (Ero1) or a fragment and/or variant thereof which has at least one Ero1 functional activity. In some instances, the genetically modified host cell is *S. cerevisiae.*

In another aspect, the recombinant polypeptide expressed in genetically modified host cell of the present invention comprises an amino acid sequence having at least 95%, 96%, 97%, 98%, 99% or 100% sequence identity to SEQ ID NO:1.

In another aspect, methods of producing a recombinant polypeptide comprising culturing a genetically modified host cell of the present invention are provided. In other aspects, the methods further comprise recovering said recombinant polypeptide from culture medium. In other aspects, a recombinant polypeptide made by said methods is provided. In another aspect, the recombinant polypeptide made by methods of the present invention comprises an amino acid sequence having 99% sequence identity to SEQ ID NO:1. In other aspects, the recombinant polypeptide comprises the amino acid sequence set forth in SEQ ID NO:1. In another aspect, the recombinant polypeptide comprises a leader sequence. In one aspect the leader sequence is a modified KEX leader sequence comprising the amino acid sequence set forth in SEQ ID NO:10. As is understood in the art host cell and growth conditions can affect the final product of recombinant protein produce by a host cell. For instance, post translation modifications can be effected by host cell type and growth conditions. These post-translation modification, including, but not limited to, glycosylation and methylation of a recombinant protein can effect such aspects as, but not limited to, protein folding and protein activity or potency of the recombinant protein produced by said host cell.

In yet another aspect of the present invention, a pharmaceutical composition comprising a recombinant polypeptide made by methods of the present invention is provided. Also provided are methods of treating a patient in need thereof, comprising administering a therapeutically effective amount of said pharmaceutical composition. In some instances, the patient has a disease or condition selected from: type I diabetes, type II diabetes, glucose intolerance, hyperglycemia, Alzheimer's disease, obesity, cardiovascular disorder, congestive heart failure, and retinopathy.

As used herein, "therapeutic polypeptide" refers to proteins, polypeptides, antibodies, peptides or fragments or variants thereof, having one or more therapeutic and/or biological activities, and in particular, at least one biological activity that is useful for treating, preventing or ameliorating a disease. Therapeutic polypeptides encompassed by the invention include but are not limited to, proteins, polypeptides, peptides, antibodies, and biologics. (The terms peptides, proteins, and polypeptides are used interchangeably herein) A non-inclusive list of biological activities that may be possessed by a therapeutic polypeptide includes, any of the GLP-1 activities described herein, enhancing the immune response, promoting angiogenesis, inhibiting angiogenesis, regulating endocrine function, regulating hematopoietic functions, stimulating nerve growth, enhancing an immune response, or inhibiting an immune response.

As used herein, a "patient" is an animal, preferably a mammal, and most preferably a human, with a disease, condition or disorder.

As used herein, a "therapeutically effective amount" refers to an amount that is effective in treating, preventing or ameliorating a disease, condition or disorder. The amount of the pharmaceutical composition of the invention which will be effective in the treatment, inhibition and prevention of a disease or disorder associated with aberrant expression and/or activity of a therapeutic polypeptide can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

As used herein, "pharmaceutical composition" comprises a therapeutic polypeptide and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound or therapeutic polypeptide, preferably in purified form, together with a suitable amount of carrier so as to provide the form for proper administration to the patient. The formulation should suit the mode of administration.

As is understood in the art, to "grow in culture" and grammatical variations thereof refers to inoculating a nutrient medium with host cells and incubating the cell culture, typically under conditions optimal or standard for growth of the particular host cell, to allow cells to grow and/or divide. As is understood in the art, the enzymatic activity of one or more enzymes produced by host cells in culture can be affected by the growth conditions of the culture. For example, the proteolytic activity of a protease produced by a host cell in culture could be decreased by altering one or more of the following conditions: pH, dissolved oxygen, temperature, osmolarity, one or more media components, specific protease inhibitors, growth time and/or rate, cell concentration, duration of culture, and/or glucose feed rate (e.g., fed batch). Addition of complex protein hydrolysates to the culture may be especially effective at inhibition of proteolysis. Moreover, the conditions may be altered at one or more specific times during the culture in such a way as to maximize the effect. Similarly, glycosylation of proteins produced in culture can be affected by similar factors. Therefore, growth conditions for reducing or increasing enzymatic activity of a host cell, such as proteolytic or glycosylation activity, in culture can be optimized by adjusting one or more of the non-limiting factors listed above.

Also, as is understood in the art production of heterologous protein and/or recombinant protein in a host cell may be increased by controlling many of the same factors noted above. In addition, the addition of factors that increase vector copy number, including, but not limited to, the addition of rapamycin to growth media, may also increase production. Other factors that may increase production include, but are not limited to, co-expression of one or more chaperon proteins, such as protein disulfide-isomerase (PDI). Additionally, hemoglobin (HB) can be co-expressed with at least one heterologous polypeptide in a host cell to enhance oxygen availability for oxidative metabolism, thus, increasing polypeptide production.

In another aspect, the recombinant polypeptide expressed from the genetically modified host cells of the present invention comprises a leader sequence. In some aspects, the leader sequence is a KEX2 leader sequence or a modified KEX2 leader sequence.

Wild type KEX leader sequence is shown below as SEQ ID NO:9.

```
                                        (SEQ ID NO: 9)
Met Lys Trp Val Ser Phe Ile Ser Leu Leu Phe Leu
Phe Ser Ser Ala Tyr Ser Arg Ser Leu Asp Lys Arg
```

In some instances a modified KEX leader sequence shown as SEQ ID NO:10 is used.

```
                                       (SEQ ID NO: 10)
Met Lys Trp Val Ser Phe Ile Ser Leu Leu Phe Leu
Phe Ser Ser Ala Tyr Ser Gly Ser Leu Asp Lys Arg
```

In some instances, the KEX leader sequence can have 90%, 91%, 92%, 93%, 94%, 95%, 96%, 97%, 98%, 99%, or 100% sequence identity to SEQ ID NO:9 over the entire sequence.

Heterologous proteins or recombinant proteins that are secreted from a host cell during production may comprise a leader sequence which facilitates secretion. Leader sequences may be modified to improve secretion and therefore overall production and recovery of heterologously expressed protein; for example different leader sequences from various secreted proteins may be operably linked to the heterologous protein and assessed for enhanced expression. Alternatively, a given leader sequence may be modified by site directed mutagenesis, or by means of a combinatorial library approach to identify an improved leader sequence variant. Chimeric leader sequences, comprising regions from two or more leader peptides, may be found to improve heterologous protein expression level.

EXAMPLES

The following examples illustrate various non-limiting aspects of this invention.

Example 1—*S. cerevisiae* Strain Overexpressing KEX2, PDI1 and ERO1

A *S. ceresiviae* strain overexpressing KEX2, PDI1 and ERO1 was constructed using a yeast host expression system (*S. cerevisiae* BXP10) developed at Delta Biotechnology Ltd. (Delta) in Nottingham, UK. BXP10 originated from *S. cerevisiae* strain AH22, obtained from ATCC, which was derived from s288c. The construction of BXP10 involved a series of random mutagenesis and targeted specific gene disruptions to increase recombinant human serum albumin (rHSA) secretion capabilities and decrease unwanted post-translational modifications.

FIG. 1 shows the creation of BXP10-KEX2-PDI1-ERO1, a strain which overexpresses KEX2, PDI1 and ERO1. Expression cassettes containing KEX2-KanMX operably linked to PGK1 promoter, PDI-HphMX operably linked to PGK1 promoter, or ERO-BsdMX operably linked to PGK1 promoter were sequentially integrated into the NTS2-2 loci (non transcribed spacer region in rDNA repeats) of BXP10, so that the following strains were created: BXP10-KEX2 (strain overexpressing KEX2), BXP10-KEX2-PDI1 (strain overexpressing KEX2 and PDI1) and BXP10-KEX2-PDI1-ERO1 (strain overexpressing KEX2, PDI1 and ERO1).

To construct the expression cassette of KEX2, KEX2 ORF, PGK1 gene promoter ($P_{PGK1}$) and ADH1 gene transcription termination sequence ($T_{ADH1}$) were amplified individually by PCR from BXP10 genomic DNA, and were assembled later using another PCR reaction (a "sewing" or "fusion" PCR reaction). The assembled $P_{PGK1}$-KEX2-$T_{ADH1}$ fragment was cloned into pRS314KanMX to generate pRS314KanMXpPGK1-KEX2. This plasmid was used as the template in a final round of PCR to add 5'- and 3'-flanking sequences (105 bp and 101 bp, respectively) which are homologous to the NTS2-2 integration sites. The resulting DNA fragment was transformed into BXP10 host strain by electroporation and plated out on plates containing G418. The G418 resistant clones were further confirmed to be positive for the site specific integration by colony PCR.

The plasmid pRS314HphMXpPGK1-PDI1 that harbors expression cassette of PDI1 was constructed by replacing KEX2 ORF and KanMX regions in pRS314KanMXpPGK1-KEX2 with PCR amplified PDI1 ORF and hygromycin B resistance marker, HphMX. This plasmid was used as the template in a final round of PCR to add 5'- and 3'-flanking sequences (105 bp and 101 bp respectively) which are homologous to the NTS2-2 integration sites. The resulting DNA fragment was transformed into BXP10-KEX2 host strains by electroporation and plated out on plates containing hygromycin B. The hygromycin B resistant clones were further confirmed to be positive for the site specific integration by colony PCR.

The ERO1 ORF was amplified from the genomic DNA of BXP10 by PCR and then was further cloned into pRS314pPGK1BsdMX to make pRS314BsdMXpPGK1-ERO1. This plasmid was used as the template in a final round of PCR to add 5'- and 3'-flanking sequences (105 bp and 101 bp respectively) which are homologous to the NTS2-2 integration sites. The resulting DNA fragment was transformed into BXP10-KEX2-PDI1 host strain by electroporation and plated out on plates containing Blasticidin S. The Blasticidin resistant clones were further confirmed to be positive for the site specific integration by colony PCR.

FIG. 2 shows the Southern blot analysis confirming integration of KEX2 and PDI1 into the NTS2-2 loci of BXP10, to create BXP10-KEX2 and BXP10-KEX2-PDI1 strains. For KEX2, the 2.6 kb band corresponds to the endogenous KEX2 copy, and the 1.6 kb band corresponds to the successfully integrated copy. For PDI1, the 1.3 kb band corresponds to the endogenous PDI1 copy and the 1.7 kb band corresponds to the successfully integrated copy.

FIG. 3 shows the Western blot analysis of PDI1 and KEX2 showing overexpression of PDI1 and KEX2 in BXP10-KEX2-PDI1 clones. Among the five BXP10-KEX2-PDI1 clones, clone #2 showed highest expression of both PDI1 and KEX2, and was therefore selected as the host strain to construct BXP10-KEX2-PDI1-ERO1.

Host strains were then transformed with the pCID3610 plasmid, which contains a recombinant fusion protein ("pCID3610 protein") consisting of two copies of human glucagon-like peptide 1 (GLP-1, fragment 7-36(A8G)) and recombinant human albumin (rHA). Each GLP-1 sequence has been modified with a glycine substituted for the naturally-occurring alanine at position 8 in order to confer resistance to proteolysis. The second GLP-1 sequence functions as a peptide spacer between the first GLP-1 sequence and rHA. pCID3610 protein is a non-glycosylated protein consisting of 645 amino acids and has a molecular weight of 72,970.4 Da. pCID3610 is described in detail in U.S. Pat. No. 7,569,384 which is incorporated herein in its entirety.

The pCID3610 plasmid was constructed at Human Genome Sciences at Rockville, Md., using the pSAC35-based expression vector. pSAC35 contains the LEU2 gene of *S. cerevisiae* as a selection marker that complements the leucine auxotrophy in BXP10. pSAC35 also contains a strong yeast promoter (PRB1), a unique cloning site (NotI), and sequence from *E. coli* plasmid pUC9 to permit cloning and propagation in *E. coli*. In addition, pSAC35 is a disintegrative vector and once it is transformed in yeast, the pUC9-derived sequences are excised by site-specific recombination. This excision is accomplished by FLP recognition targets (FRT) and the expression of the yeast FLP ("flip") recombinase from the 2 micron plasmid. Other segments in pSAC35 include the REP1 and REP2 regions of the D-gene. The REP1 and REP2 genes encode products that help regulate plasmid copy number and also play a role in plasmid segregation during cell division. The product of the D-gene increases FLP expression by relieving the repression caused by REP1 and REP2. pCID3610 is described in detail in U.S. Pat. No. 7,569,384 which is incorporated herein in its entirety.

The full-length cDNA of human albumin (HA) was isolated from a human cDNA library and cloned into a plasmid, pAT153ALB, in the laboratory of Dr. F. E. Baralle at Oxford University, U.K. The pAT153ALB was subsequently modified by Delta by introducing novel restriction sites to ease cloning into pSAC35.

The expression vector plasmid, pCID3610, was constructed from pSAC35 by introduction of the GLP-1-rHSA fusion gene assembled as follows. First, synthetic genes were prepared encoding the leader peptide and a mature GLP-1 variant having a single A to G substitution at position 2 of the mature peptide. The variant GLP-1 peptide was reverse translated using optimal codons for yeast, and tandem copies were synthesized via PCR using overlapping oligonucleotides. This synthetic gene was used as the template in a second round of PCR to add 5'- and 3'-restriction sites to permit its cloning into the 5'-end of the rHSA gene. Finally, a signal peptide encoding sequence was ligated onto the 5' end of the GLP-1 construct. The resulting fragment was ligated into pSAC35 at the unique NotI site and transformed into DH5α resulting in the expression vector pCID3610. The nucleotide sequence of pCID3610 was confirmed. Then, pCID3610 was transformed into DH5α again for further amplification and isolation of the plasmid DNA.

To construct the BXP10-KEX2-PDI1-ERO1 strain expressing pCID3610, pCID3610 was transformed into BXP10-KEX2-PDI-ERO1 by electroporation, and cells were then plated onto ESFM2 agarose plates, and Leu+ colonies were selected after 4 days of incubating the plates at 30 C. Twelve (12) colonies of transformants were further streaked on ESFM2 agarose plates to obtain single clones. One colony from each streak was inoculated in ESFM2 medium for screening using 24 deep-well culture plates.

After 3 day incubation with agitation, supernatant from each of the 12 clonal cultures were analyzed on SDS-PAGE. FIG. 4 shows the SDS-PAGE of the 12 supernatant samples. Then, 4 clones from the 12 clones (clone #2, clone #8, clone #10 and clone #12) were selected for further fermentation tests (selected clones marked with arrows in FIG. 4). Because of variable evaporation of media from each well on the culture plate, the four clones were selected based on consideration of the final volume of each culture at the end of growth, OD measurement of cell culture, and band intensity on the SDS-PAGE gel.

The four selected clones were then run in DASGIP mini-bioreactors using a fermentation program, and the resulting titer yields and protein quality compared to those of BXP10 expressing pCID3610, a host strain which does not overexpress KEX2, PDI1 and ERO1. FIG. 5 shows analysis of the titer yield and protein quality of protein produced in the fermentation run. Protein quality is measured by the percentage of protein product that has an extra 6 amino acids (6-AA) at the N-terminus due to inefficient leader sequence cleavage. Clone #2 and clone #8 showed significant increase in pCID3610 protein concentration compared to BXP10 expressing pCID3610, which generated only up to 1.6 g/L pCID3610 protein under the same fermentation conditions (data for BXP10 expressing pCID3610 not shown in FIG. 5). Further, the levels of 6-AA in all clones (<1% of protein product having extra 6-AA) were significantly decreased compared to 6-AA levels in BXP10 expressing pCID3610 protein, which had 4-7% of the protein product having extra 6-AA (data for BXP10 expressing pCID3610 not shown in FIG. 5). These results suggest that overexpression of KEX2, PDI1 and ERO1 has greatly improved the host strain (BXP10) to produce more of better quality pCID3610 protein.

Although the titer yield and 6-AA levels in clone #2 and clone #8 were comparable, clone #8 was selected as the lead clone because it showed slightly better results in the fermentation run. To confirm the improved titer yield and protein quality of pCID3610, clone #8 was run in a 15 L fermentor. The average titer yield from four (4) batches of runs was 2.5 g/L, which is a 40-50% increase from the titer yield using BXP10 expressing pCID3610.

Two separate frozen stocks of BXP10-KEX2-PD11-ERO1 clone #8 were then prepared. The first frozen stock ("Research Cell Bank Vial") was prepared by growing clone #8 in 200 ml of ESFM2 medium that contained all 3 antibiotics (G418, hygromycin and blasticidin). When the cell culture reached $OD_{600}$~3.0, cells were harvested, washed, resuspended and aliquoted to make 20% trehalose frozen stocks.

Cells from the Research Cell Bank Vial were then thawed and grown in ESFM2 medium at 30° C. and 250 rpm. Culture density was monitored by measuring $OD_{600}$ of the culture. FIG. 6 shows the growth curve of the cells. At about $OD_{600}$=2.54, cells were harvested, washed and resuspended to make a second frozen stock ("Pre-Master Cell Bank"). FIG. 7 shows the growth curve of cells from the Pre-Master Cell Bank.

The stability of BXP10-KEX2-PDI1-ERO1 clone #8 was then tested by in vitro cell age and 15 L production studies. Briefly, clone #8 cells from the Pre-Master Cell Bank were passaged through seven consecutive shaking flask steps, which corresponds to approximately 51 cell generations. Then, the cells were inoculated in 15 L fermentors and run through a fermentation program. This fermentation process added another 14 generations. The supernatant titer yield reached 5.3 g/L with 6-AA levels less than 1.5%. The data indicated that BXP10-KEX2-PDI1-ERO1 clone #8 is stably producing pCID3610 protein after about 65 generations.

To construct the expression cassette of KEX2, the PGK1 gene promoter (Ppm), KEX2 ORF and ADH1 gene transcription termination sequence ($T_{ADH1}$) were amplified individually by PCR from BXP10 genomic DNA respectively, and were assembled later using another PCR reaction (a "sewing" or "fusion" PCR reaction). The assembled Ppm-KEX2-$T_{ADH1}$ fragment was cloned into pRS314KanMX to generate pRS314KanMXpPGK1-KEX2. This plasmid was then used as a template in a final round of PCR to add 5'- and 3'-flanking sequences (105 bp and 101 bp, respectively) which are homologous to the NTS2-2 integration sites. The resulting PCR fragment was transformed into BXP10 host strain by electroporation and plated out on plates containing G418. The G418 resistant clones were further confirmed to be positive for the site specific integration by colony PCR.

The PDI1 ORF was amplified from BXP10 genomic DNA. This DNA fragment and Hygromycin B resistance marker, HphMX were used to replace KEX2 ORF and KanMX regions in pRS314KanMXpPGK1-KEX2, which resulted in plasmid pRS314HphMXpPGK1-PD11. This plasmid was then used as the template in a final round of PCR to add 5'- and 3'-flanking sequences (105 bp and 101 bp respectively) which are homologous to the NTS2-2 integration sites. The resulting DNA fragment was transformed into BXP10-KEX2 host strains by electroporation and plated out on plates containing hygromycin B. The hygromycin B resistant clones were further confirmed to be positive for the site specific integration by colony PCR.

Similarly, the ERO1 ORF was amplified from the genomic DNA of BXP10 by PCR and then was further cloned into pRS314pPGK1BsdMX to make pRS314BsdMXpPGK1-ERO1. This plasmid was used as the template in a final round of PCR to add 5'- and 3'-flanking sequences (105 bp and 101 bp respectively) which are homologous to the NTS2-2 integration sites. The resulting DNA fragment was transformed into BXP10-KEX2-PDI1 host strain by electroporation and plated out on plates containing Blasticidin S. The Blasticidin resistant clones were further confirmed to be positive for the site specific integration by colony PCR.

We claim:

1. A host cell comprising at least one heterologous nucleic acid sequence encoding a Killer Expression protease (Kex2p) having at least 90% sequence identity to the amino acid sequence set forth in SEQ ID NO: 4, and at least one heterologous nucleic acid sequence encoding a Protein Disulfide-Isomerase (Pdi1) having at least 90% sequence identity to the amino acid sequence set forth in SEQ ID NO: 6, and at least one heterologous nucleic acid sequence encoding an Endoplasmic Reticulum Oxidoreductin (Ero1) having at least 90% sequence identity to the amino acid sequence set forth in SEQ ID NO: 8.

2. The host cell of claim 1, wherein said host cell expresses or overexpresses at least one gene product of said at least one heterologous nucleic acid sequence encoding a protein selected from: a Kex2p protein having at least 90% sequence identity to the amino acid sequence set forth in SEQ ID NO: 4, a Pdi1 protein having at least 90% sequence identity to the amino acid sequence set forth in SEQ ID NO: 6 and a Ero1 protein having at least 90% sequence identity to the amino acid sequence set forth in SEQ ID NO: 8 when said host cell is grown in culture.

3. The host cell of claim 1 wherein said host cell is a yeast cell.

4. The host cell of claim 3, wherein the genera of said yeast cell is selected from the group consisting of: *Saccharomyces, Kluyveromyces, Candida, Pichia, Schizosaccharomyces, Hansenula, Kloeckera, Schwanniomyces*, and *Yarrowia.*

5. The host cell of claim 4 wherein said host cell is *Saccharomyces cerevisiae.*

6. The host cell of claim 1, wherein said host cell further comprises at least one of the following genetic modifications: pep4 protease knockout, lower ubc4 and/or ubc5 activity compared with wild type host cell, yps1 knockout, hsp150 knockout, and pmt1 knockout.

7. The host cell of claim 1 comprising at least one nucleic acid encoding a recombinant polypeptide.

8. The host cell of claim 7 wherein said recombinant polypeptide has at least one disulfide bond.

9. The host cell of claim 7 wherein said recombinant polypeptide is an albumin fusion protein.

10. The host cell of claim 7 wherein said recombinant polypeptide has a polypeptide having at least 95% sequence identity to the amino acid sequence set forth in SEQ ID NO:1.

11. The host cell of claim 7 wherein the recombinant polypeptide comprises an amino acid sequence set forth in SEQ ID NO:1.

12. The host cell of claim 1 wherein said Kex2p is encoded by the nucleic acid sequence set forth in SEQ ID NO:3.

13. The host cell of claim 1 wherein said Pdi1 is encoded by the nucleic acid sequence set forth in SEQ ID NO:5.

14. The host cell of claim 1 wherein said Ero1 is encoded by the nucleic acid sequence set forth in SEQ ID NO:7.

15. The host cell of claim 1 further comprising at least one nucleic acid encoding a recombinant polypeptide wherein said host cell increases the titre yield of said recombinant polypeptide when grown in culture compared with a host cell of the same species and genetic modifications but which does not comprise at least one heterologous nucleic acid sequence encoding a Killer Expression protease (Kex2p) having at least 90% sequence identity to the amino acid sequence set forth in SEQ ID NO: 4, at least one heterologous nucleic acid sequence encoding a Protein Disulfide-Isomerase (Pdi1) having at least 90% sequence identity to the amino acid sequence set forth in SEQ ID NO: 6, and at least one heterologous nucleic acid sequence encoding a Endoplasmic Reticulum Oxidoreductin (Ero1) having at least 90% sequence identity to the amino acid sequence set forth in SEQ ID NO: 8.

16. A method of producing a recombinant polypeptide comprising culturing a host cell of claim 7 and recovering said recombinant polypeptide from culture medium.

17. A host cell which overexpresses a Killer Expression protease (Kex2p) having at least 90% sequence identity to the amino acid sequence set forth in SEQ ID NO:4, a Protein Disulfide-Isomerase (Pdi1) having at least 90% sequence identity to the amino acid sequence set forth in SEQ ID NO: 6, and a Endoplasmic Reticulum Oxidoreductin (Ero11 having at least 90% sequence identity to the amino acid sequence set forth in SEQ ID NO: 8 when said host cell is grown in culture compared to wild type host cell wherein said wild type host cell is the same species and grown in the same culture conditions.

* * * * *

SEQUENCE LISTING

```
<160> NUMBER OF SEQ ID NOS: 10

<210> SEQ ID NO 1
<211> LENGTH: 651
<212> TYPE: PRT
<213> ORGANISM: Artificial Sequence
<220> FEATURE:
<223> OTHER INFORMATION: heterologous polypeptide

<400> SEQUENCE: 1

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
    290                 295                 300

Cys Cys His Gly Asp Leu Leu Glu Cys Ala Asp Asp Arg Ala Asp Leu
305                 310                 315                 320
```

-continued

Ala Lys Tyr Ile Cys Glu Asn Gln Asp Ser Ile Ser Ser Lys Leu Lys
325 330 335

Glu Cys Cys Glu Lys Pro Leu Leu Glu Lys Ser His Cys Ile Ala Glu
340 345 350

Val Glu Asn Asp Glu Met Pro Ala Asp Leu Pro Ser Leu Ala Ala Asp
355 360 365

Phe Val Glu Ser Lys Asp Val Cys Lys Asn Tyr Ala Glu Ala Lys Asp
370 375 380

Val Phe Leu Gly Met Phe Leu Tyr Glu Tyr Ala Arg Arg His Pro Asp
385 390 395 400

Tyr Ser Val Val Leu Leu Leu Arg Leu Ala Lys Thr Tyr Glu Thr Thr
405 410 415

Leu Glu Lys Cys Cys Ala Ala Ala Asp Pro His Glu Cys Tyr Ala Lys
420 425 430

Val Phe Asp Glu Phe Lys Pro Leu Val Glu Glu Pro Gln Asn Leu Ile
435 440 445

Lys Gln Asn Cys Glu Leu Phe Glu Gln Leu Gly Glu Tyr Lys Phe Gln
450 455 460

Asn Ala Leu Leu Val Arg Tyr Thr Lys Lys Val Pro Gln Val Ser Thr
465 470 475 480

Pro Thr Leu Val Glu Val Ser Arg Asn Leu Gly Lys Val Gly Ser Lys
485 490 495

Cys Cys Lys His Pro Glu Ala Lys Arg Met Pro Cys Ala Glu Asp Tyr
500 505 510

Leu Ser Val Val Leu Asn Gln Leu Cys Val Leu His Glu Lys Thr Pro
515 520 525

Val Ser Asp Arg Val Thr Lys Cys Cys Thr Glu Ser Leu Val Asn Arg
530 535 540

Arg Pro Cys Phe Ser Ala Leu Glu Val Asp Glu Thr Tyr Val Pro Lys
545 550 555 560

Glu Phe Asn Ala Glu Thr Phe Thr Phe His Ala Asp Ile Cys Thr Leu
565 570 575

Ser Glu Lys Glu Arg Gln Ile Lys Lys Gln Thr Ala Leu Val Glu Leu
580 585 590

Val Lys His Lys Pro Lys Ala Thr Lys Glu Gln Leu Lys Ala Val Met
595 600 605

Asp Asp Phe Ala Ala Phe Val Glu Lys Cys Cys Lys Ala Asp Asp Lys
610 615 620

Glu Thr Cys Phe Ala Glu Glu Gly Lys Lys Leu Val Ala Ala Ser Gln
625 630 635 640

Ala Ala Leu Gly Leu Ser Glu Gln Ile Asp Asn
645 650

<210> SEQ ID NO 2
<211> LENGTH: 31
<212> TYPE: PRT
<213> ORGANISM: Artificial Sequence
<220> FEATURE:
<223> OTHER INFORMATION: albumin fusion protein
<220> FEATURE:
<221> NAME/KEY: VARIANT
<222> LOCATION: 31
<223> OTHER INFORMATION: Xaa = Any Amino Acid

<400> SEQUENCE: 2

His Ala Glu Gly Thr Phe Thr Ser Asp Val Ser Ser Tyr Leu Glu Gly

-continued

```
 1               5                   10                  15

Gln Ala Ala Lys Glu Phe Ile Ala Trp Leu Val Lys Gly Arg Xaa
            20                  25                  30
```

<210> SEQ ID NO 3
<211> LENGTH: 2445
<212> TYPE: DNA
<213> ORGANISM: Artificial Sequence
<220> FEATURE:
<223> OTHER INFORMATION: S. cerevisiae

<400> SEQUENCE: 3

```
atgaaagtga ggaaatatat tactttatgc ttttggtggg ccttttcaac atccgctctt     60

gtatcatcac aacaaattcc attgaaggac catacgtcac gacagtattt tgctgtagaa    120

agcaatgaaa cattatcccg cttggaggaa atgcatccaa attggaaata tgaacatgat    180

gttcgagggc taccaaacca ttatgttttt tcaaaagagt tgctaaaatt gggcaaaaga    240

tcatcattag aagagttaca gggggataac aacgaccaca tattatctgt ccatgattta    300

ttcccgcgta acgacctatt taagagacta ccggtgcctg ctccaccaat ggactcaagc    360

ttgttaccgg taaaagaagc tgaggataaa ctcagcataa atgatccgct tttgagaggg    420

cagtggcact tggtcaatcc aagttttcct ggcagtgata taaatgttct tgatctgtgg    480

tacaataata ttacaggcgc aggggtcgtg gctgccattg ttgatgatgg ccttgactac    540

gaaaatgaag acttgaagga taatttttgc gctgaaggtt cttgggattt caacgacaat    600

accaatttac ctaaaccaag attatctgat gactaccatg gtacgagatg tgcaggtgaa    660

atagctgcca aaaaaggtaa caatttttgc ggtgtcgggg taggttacaa cgctaaaatc    720

tcaggcataa gaatcttatc cggtgatatc actacggaag atgaagctgc gtccttgatt    780

tatggtctag acgtaaacga tatatattca tgctcatggg gtcccgctga tgacggaaga    840

catttacaag gccctagtga cctggtgaaa aaggctttag taaaaggtgt tactgaggga    900

agagattcca aaggagcgat ttacgttttt gccagtggaa atggtggaac tcgtggtgat    960

aattgcaatt acgacggcta tactaattcc atatattcta ttactattgg ggctattgat   1020

cacaaagatc tacatcctcc ttattccgaa ggttgttccg ccgtcatggc agtcacgtat   1080

tcttcaggtt caggcgaata tattcattcg agtgatatca acggcagatg cagtaatagc   1140

cacggtggaa cgtctgcggc tgctccatta gctgccggtg tttacacttt gttactagaa   1200

gccaacccaa acctaacttg gagagacgta cagtatttat caatcttgtc tgcggtaggg   1260

ttagaaaaga acgctgacgg agattggaga gatagcgcca tggggaagaa atactctcat   1320

cgctatggct ttggtaaaat cgatgcccat aagttaattg aaatgtccaa gacctgggag   1380

aatgttaacg cacaaacctg gttttacctg ccaacattgt atgtttccca gtccacaaac   1440

tccacggaag agacattaga atccgtcata accatatcag aaaaaagtct tcaagatgct   1500

aacttcaaga gaattgagca cgtcacggta actgtagata ttgatacaga aattagggga   1560

actacgactg tcgatttaat atcaccagcg ggataatttt caaaccttgg cgttgtaaga   1620

ccaagagatg tttcatcaga gggattcaaa gactggacat tcatgtctgt agcacattgg   1680

ggtgagaacg gcgtaggtga ttggaaaatc aaggttaaga caacagaaaa tggacacagg   1740

attgacttcc acagttggag gctgaagctc tttggggaat ccattgattc atctaaaaca   1800

gaaactttcg tctttggaaa cgataaagag gaggttgaac cagctgctac agaaagtacc   1860

gtatcacaat attctgccag ttcaacttct atttccatca gcgctacttc tacatcttct   1920
```

atctcaattg gtgtggaaac gtcggccatt ccccaaacga ctactgcgag taccgatcct 1980
gattctgatc caaacactcc taaaaaactt tcctctccta ggcaagccat gcattatttt 2040
ttaacaatat ttttgattgg cgccacattt ttggtgttat acttcatgtt ttttatgaaa 2100
tcaaggagaa ggatcagaag gtcaagagcg gaaacgtatg aattcgatat cattgataca 2160
gactctgagt acgattctac tttggacaat ggaacttccg gaattactga gcccgaagag 2220
gttgaggact tcgattttga tttgtccgat gaagaccatc ttgcaagttt gtcttcatca 2280
gaaaacggtg atgctgaaca tacaattgat agtgtactaa caaacgaaaa tccatttagt 2340
gaccctataa agcaaaagtt cccaaatgac gccaacgcag aatctgcttc caataaatta 2400
caagaattac agcctgatgt tcctccatct tccggacgat cgtga 2445

<210> SEQ ID NO 4
<211> LENGTH: 814
<212> TYPE: PRT
<213> ORGANISM: Artificial Sequence
<220> FEATURE:
<223> OTHER INFORMATION: S. cerevisiae

<400> SEQUENCE: 4

Met Lys Val Arg Lys Tyr Ile Thr Leu Cys Phe Trp Trp Ala Phe Ser
1 5 10 15

Thr Ser Ala Leu Val Ser Ser Gln Gln Ile Pro Leu Lys Asp His Thr
20 25 30

Ser Arg Gln Tyr Phe Ala Val Glu Ser Asn Glu Thr Leu Ser Arg Leu
35 40 45

Glu Glu Met His Pro Asn Trp Lys Tyr Glu His Asp Val Arg Gly Leu
50 55 60

Pro Asn His Tyr Val Phe Ser Lys Glu Leu Leu Lys Leu Gly Lys Arg
65 70 75 80

Ser Ser Leu Glu Glu Leu Gln Gly Asp Asn Asn Asp His Ile Leu Ser
85 90 95

Val His Asp Leu Phe Pro Arg Asn Asp Leu Phe Lys Arg Leu Pro Val
100 105 110

Pro Ala Pro Pro Met Asp Ser Ser Leu Leu Pro Val Lys Glu Ala Glu
115 120 125

Asp Lys Leu Ser Ile Asn Asp Pro Leu Phe Glu Arg Gln Trp His Leu
130 135 140

Val Asn Pro Ser Phe Pro Gly Ser Asp Ile Asn Val Leu Asp Leu Trp
145 150 155 160

Tyr Asn Asn Ile Thr Gly Ala Gly Val Val Ala Ala Ile Val Asp Asp
165 170 175

Gly Leu Asp Tyr Glu Asn Glu Asp Leu Lys Asp Asn Phe Cys Ala Glu
180 185 190

Gly Ser Trp Asp Phe Asn Asp Asn Thr Asn Leu Pro Lys Pro Arg Leu
195 200 205

Ser Asp Asp Tyr His Gly Thr Arg Cys Ala Gly Glu Ile Ala Ala Lys
210 215 220

Lys Gly Asn Asn Phe Cys Gly Val Gly Val Gly Tyr Asn Ala Lys Ile
225 230 235 240

Ser Gly Ile Arg Ile Leu Ser Gly Asp Ile Thr Thr Glu Asp Glu Ala
245 250 255

Ala Ser Leu Ile Tyr Gly Leu Asp Val Asn Asp Ile Tyr Ser Cys Ser
260 265 270

-continued

```
Trp Gly Pro Ala Asp Asp Gly Arg His Leu Gln Gly Pro Ser Asp Leu
        275                 280                 285

Val Lys Lys Ala Leu Val Lys Gly Val Thr Glu Gly Arg Asp Ser Lys
    290                 295                 300

Gly Ala Ile Tyr Val Phe Ala Ser Gly Asn Gly Gly Thr Arg Gly Asp
305                 310                 315                 320

Asn Cys Asn Tyr Asp Gly Tyr Thr Asn Ser Ile Tyr Ser Ile Thr Ile
                325                 330                 335

Gly Ala Ile Asp His Lys Asp Leu His Pro Pro Tyr Ser Glu Gly Cys
            340                 345                 350

Ser Ala Val Met Ala Val Thr Tyr Ser Ser Gly Ser Gly Glu Tyr Ile
        355                 360                 365

His Ser Ser Asp Ile Asn Gly Arg Cys Ser Asn Ser His Gly Gly Thr
    370                 375                 380

Ser Ala Ala Ala Pro Leu Ala Ala Gly Val Tyr Thr Leu Leu Leu Glu
385                 390                 395                 400

Ala Asn Pro Asn Leu Thr Trp Arg Asp Val Gln Tyr Leu Ser Ile Leu
                405                 410                 415

Ser Ala Val Gly Leu Glu Lys Asn Ala Asp Gly Asp Trp Arg Asp Ser
            420                 425                 430

Ala Met Gly Lys Lys Tyr Ser His Arg Tyr Gly Phe Gly Lys Ile Asp
        435                 440                 445

Ala His Lys Leu Ile Glu Met Ser Lys Thr Trp Glu Asn Val Asn Ala
    450                 455                 460

Gln Thr Trp Phe Tyr Leu Pro Thr Leu Tyr Val Ser Gln Ser Thr Asn
465                 470                 475                 480

Ser Thr Glu Glu Thr Leu Glu Ser Val Ile Thr Ile Ser Glu Lys Ser
                485                 490                 495

Leu Gln Asp Ala Asn Phe Lys Arg Ile Glu His Val Thr Val Thr Val
            500                 505                 510

Asp Ile Asp Thr Glu Ile Arg Gly Thr Thr Thr Val Asp Leu Ile Ser
        515                 520                 525

Pro Ala Gly Ile Ile Ser Asn Leu Gly Val Val Arg Pro Arg Asp Val
    530                 535                 540

Ser Ser Glu Gly Phe Lys Asp Trp Thr Phe Met Ser Val Ala His Trp
545                 550                 555                 560

Gly Glu Asn Gly Val Gly Asp Trp Lys Ile Lys Val Lys Thr Thr Glu
                565                 570                 575

Asn Gly His Arg Ile Asp Phe His Ser Trp Arg Leu Lys Leu Phe Gly
            580                 585                 590

Glu Ser Ile Asp Ser Ser Lys Thr Glu Thr Phe Val Phe Gly Asn Asp
        595                 600                 605

Lys Glu Glu Val Glu Pro Ala Ala Thr Glu Ser Thr Val Ser Gln Tyr
    610                 615                 620

Ser Ala Ser Ser Thr Ser Ile Ser Ile Ser Ala Thr Ser Thr Ser Ser
625                 630                 635                 640

Ile Ser Ile Gly Val Glu Thr Ser Ala Ile Pro Gln Thr Thr Thr Ala
                645                 650                 655

Ser Thr Asp Pro Asp Ser Asp Pro Asn Thr Pro Lys Lys Leu Ser Ser
            660                 665                 670

Pro Arg Gln Ala Met His Tyr Phe Leu Thr Ile Phe Leu Ile Gly Ala
        675                 680                 685

Thr Phe Leu Val Leu Tyr Phe Met Phe Phe Met Lys Ser Arg Arg Arg
```

```
    690                 695                 700

Ile Arg Arg Ser Arg Ala Glu Thr Tyr Glu Phe Asp Ile Ile Asp Thr
705                 710                 715                 720

Asp Ser Glu Tyr Asp Ser Thr Leu Asp Asn Gly Thr Ser Gly Ile Thr
                725                 730                 735

Glu Pro Glu Glu Val Glu Asp Phe Asp Phe Asp Leu Ser Asp Glu Asp
            740                 745                 750

His Leu Ala Ser Leu Ser Ser Ser Glu Asn Gly Asp Ala Glu His Thr
        755                 760                 765

Ile Asp Ser Val Leu Thr Asn Glu Asn Pro Phe Ser Asp Pro Ile Lys
    770                 775                 780

Gln Lys Phe Pro Asn Asp Ala Asn Ala Glu Ser Ala Ser Asn Lys Leu
785                 790                 795                 800

Gln Glu Leu Gln Pro Asp Val Pro Pro Ser Ser Gly Arg Ser
                805                 810


<210> SEQ ID NO 5
<211> LENGTH: 1569
<212> TYPE: DNA
<213> ORGANISM: Artificial Sequence
<220> FEATURE:
<223> OTHER INFORMATION: S. cerevisiae

<400> SEQUENCE: 5

atgaagtttt ctgctggtgc cgtcctgtca tggtcctccc tgctgctcgc ctcctctgtt     60

ttcgcccaac aagaggctgt ggcccctgaa gactccgctg tcgttaagtt ggccaccgac    120

tccttcaatg agtacattca gtcgcacgac ttggtgcttg cggagttttt tgctccatgg    180

tgtggccact gtaagaacat ggctcctgaa tacgttaaag ccgccgagac tttagttgag    240

aaaaacatta ccttggccca gatcgactgt actgaaaacc aggatctgtg tatggaacac    300

aacattccag ggttcccaag cttgaagatt ttcaaaaaca gcgatgttaa caactcgatc    360

gattacgagg gacctagaac tgccgaggcc attgtccaat tcatgatcaa gcaaagccaa    420

ccggctgtcg ccgttgttgc tgatctacca gcttaccttg ctaacgagac ttttgtcact    480

ccagttatcg tccaatccgg taagattgac gccgacttca acgccacctt ttactccatg    540

gccaacaaac acttcaacga ctacgacttt gtctccgctg aaaacgcaga cgatgatttc    600

aagctttcta tttacttgcc ctccgccatg gacgagcctg tagtatacaa cggtaagaaa    660

gccgatatcg ctgacgctga tgtttttgaa aaatggttgc aagtggaagc cttgccctac    720

tttggtgaaa tcgacggttc cgttttcgcc caatacgtcg aaagcggttt gcctttgggt    780

tacttattct acaatgacga ggaagaattg gaagaataca agcctctctt taccgagttg    840

gccaaaaaga acagaggtct aatgaacttt gttagcatcg atgccagaaa attcggcaga    900

cacgccggca acttgaacat gaaggaacaa ttccctctat ttgccatcca cgacatgact    960

gaagacttga agtacggttt gcctcaactc tctgaagagg cgtttgacga attgagcgac   1020

aagatcgtgt tggagtctaa ggctattgaa tctttggtta aggacttctt gaaaggtgat   1080

gcctccccaa tcgtgaagtc ccaagagatc ttcgagaacc aagattcctc tgtcttccaa   1140

ttggtcggta agaaccatga cgaaatcgtc aacgacccaa agaaggacgt tcttgttttg   1200

tactatgccc catggtgtgg tcactgtaag agattggccc caacttacca agaactagct   1260

gatacctacg ccaacgccac atccgacgtt ttgattgcta aactagacca cactgaaaac   1320

gatgtcagag gcgtcgtaat tgaaggttac ccaacaatcg tcttataccc aggtggtaag   1380
```

```
aagtccgaat ctgttgtgta ccaaggttca agatccttgg actctttatt cgacttcatc   1440

aaggaaaacg gtcacttcga cgtcgacggt aaggccttgt acgaagaagc ccaggaaaaa   1500

gctgctgagg aagccgatgc tgacgctgaa ttggctgacg aagaagatgc cattcacgat   1560

gaattgtaa                                                           1569
```

<210> SEQ ID NO 6
<211> LENGTH: 522
<212> TYPE: PRT
<213> ORGANISM: Artificial Sequence
<220> FEATURE:
<223> OTHER INFORMATION: S. cerevisiae

<400> SEQUENCE: 6

```
Met Lys Phe Ser Ala Gly Ala Val Leu Ser Trp Ser Ser Leu Leu Leu
 1               5                  10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
    50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Glu Leu Glu Glu
            260                 265                 270

Tyr Lys Pro Leu Phe Thr Glu Leu Ala Lys Lys Asn Arg Gly Leu Met
        275                 280                 285

Asn Phe Val Ser Ile Asp Ala Arg Lys Phe Gly Arg His Ala Gly Asn
    290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
```

-continued

```
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
        355                 360                 365

Glu Ile Phe Glu Asn Gln Asp Ser Ser Val Phe Gln Leu Val Gly Lys
    370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
        435                 440                 445

Gly Tyr Pro Thr Ile Val Leu Tyr Pro Gly Gly Lys Lys Ser Glu Ser
    450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Glu Ala Asp Ala Asp Ala Glu Leu Ala
            500                 505                 510

Asp Glu Glu Asp Ala Ile His Asp Glu Leu
        515                 520
```

<210> SEQ ID NO 7
<211> LENGTH: 1692
<212> TYPE: DNA
<213> ORGANISM: Artificial Sequence
<220> FEATURE:
<223> OTHER INFORMATION: S. cerevisiae

<400> SEQUENCE: 7

```
atgagattaa gaaccgccat tgccacactg tgcctcacgg cttttacatc tgcaacttca     60

aacaatagct acatcgccac cgaccaaaca caaaatgcct ttaatgacac tcacttttgt    120

aaggtcgaca ggaatgatca cgttagtccc agttgtaacg taacattcaa tgaattaaat    180

gccataaatg aaaacattag agatgatctt tcggcgttat taaaatctga tttcttcaaa    240

tactttcggc tggatttata caagcaatgt tcattttggg acgccaacga tggtctgtgc    300

ttaaaccgcg cttgctctgt tgatgtcgta gaggactggg atacactgcc tgagtactgg    360

cagcctgaga tcttgggtag tttcaataat gatacaatga aggaagcgga tgatagcgat    420

gacgaatgta agttcttaga tcaactatgt caaaccagta aaaaacctgt agatatcgaa    480

gacaccatca actactgtga tgtaaatgac tttaacggta aaaacgccgt tctgattgat    540

ttaacagcaa atccggaacg atttacaggt tatggtggta agcaagctgg tcaaatttgg    600

tctactatct accaagacaa ctgttttaca attggcgaaa ctggtgaatc attggccaaa    660

gatgcatttt atagacttgt atccggtttc catgcctcta tcggtactca cttatcaaag    720

gaatatttga acacgaaaac tggtaaatgg gagcccaatc tggatttgtt tatggcaaga    780

atcgggaact ttcctgatag agtgacaaac atgtatttca attatgctgt tgtagctaag    840

gctctctgga aaattcaacc atatttacca gaattttcat tctgtgatct agtcaataaa    900

gaaatcaaaa acaaaatgga taacgttatt tcccagctgg acacaaaaat ttttaacgaa    960
```

```
gacttagttt ttgccaacga cctaagtttg actttgaagg acgaattcag atctcgcttc   1020

aagaatgtca cgaagattat ggattgtgtg caatgtgata gatgtagatt gtggggcaaa   1080

attcaaacta ccggttacgc aactgccttg aaaattttgt ttgaaatcaa cgacgctgat   1140

gaattcacca aacaacatat tgttggtaag ttaaccaaat atgagttgat tgcactatta   1200

cagactttcg gtagattatc tgaatctatt gaatctgtta acatgttcga aaaaatgtac   1260

gggaaaaggt taaacggttc tgaaaacagg ttaagctcat tcttccaaaa taacttcttc   1320

aacattttga aggaggcagg caaatcgatt cgttacacca tagagaacat caattccact   1380

aaagaaggaa agaaaaagac taacaattct caatcacatg tatttgatga tttaaaaatg   1440

cccaaagcag aaatagttcc aaggccctct aacggtacag taaataaatg gaagaaagct   1500

tggaatactg aagttaacaa cgttttagaa gcattcagat ttatttatag aagctatttg   1560

gatttaccca ggaacatctg ggaattatct ttgatgaagg tatacaaatt ttggaataaa   1620

ttcatcggtg ttgctgatta cgttagtgag gagacacgag agcctatttc ctataagcta   1680

gatatacaat aa                                                       1692


<210> SEQ ID NO 8
<211> LENGTH: 563
<212> TYPE: PRT
<213> ORGANISM: Artificial Sequence
<220> FEATURE:
<223> OTHER INFORMATION: S. cerevisiae

<400> SEQUENCE: 8

Met Arg Leu Arg Thr Ala Ile Ala Thr Leu Cys Leu Thr Ala Phe Thr
1               5                   10                  15

Ser Ala Thr Ser Asn Asn Ser Tyr Ile Ala Thr Asp Gln Thr Gln Asn
            20                  25                  30

Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
    50                  55                  60

Asn Ile Arg Asp Asp Leu Ser Ala Leu Leu Lys Ser Asp Phe Phe Lys
65                  70                  75                  80

Tyr Phe Arg Leu Asp Leu Tyr Lys Gln Cys Ser Phe Trp Asp Ala Asn
                85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Asp Ser Asp Asp Glu Cys Lys
    130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr
    210                 215                 220
```

-continued

```
Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
                245                 250                 255

Phe Met Ala Arg Ile Gly Asn Phe Pro Asp Arg Val Thr Asn Met Tyr
            260                 265                 270

Phe Asn Tyr Ala Val Val Ala Lys Ala Leu Trp Lys Ile Gln Pro Tyr
        275                 280                 285

Leu Pro Glu Phe Ser Phe Cys Asp Leu Val Asn Lys Glu Ile Lys Asn
    290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
                325                 330                 335

Arg Ser Arg Phe Lys Asn Val Thr Lys Ile Met Asp Cys Val Gln Cys
            340                 345                 350

Asp Arg Cys Arg Leu Trp Gly Lys Ile Gln Thr Thr Gly Tyr Ala Thr
        355                 360                 365

Ala Leu Lys Ile Leu Phe Glu Ile Asn Asp Ala Asp Glu Phe Thr Lys
    370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
                405                 410                 415

Glu Lys Met Tyr Gly Lys Arg Leu Asn Gly Ser Glu Asn Arg Leu Ser
            420                 425                 430

Ser Phe Phe Gln Asn Asn Phe Phe Asn Ile Leu Lys Glu Ala Gly Lys
        435                 440                 445

Ser Ile Arg Tyr Thr Ile Glu Asn Ile Asn Ser Thr Lys Glu Gly Lys
    450                 455                 460

Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
                485                 490                 495

Trp Lys Lys Ala Trp Asn Thr Glu Val Asn Asn Val Leu Glu Ala Phe
            500                 505                 510

Arg Phe Ile Tyr Arg Ser Tyr Leu Asp Leu Pro Arg Asn Ile Trp Glu
        515                 520                 525

Leu Ser Leu Met Lys Val Tyr Lys Phe Trp Asn Lys Phe Ile Gly Val
    530                 535                 540

Ala Asp Tyr Val Ser Glu Glu Thr Arg Glu Pro Ile Ser Tyr Lys Leu
545                 550                 555                 560

Asp Ile Gln


<210> SEQ ID NO 9
<211> LENGTH: 24
<212> TYPE: PRT
<213> ORGANISM: Artificial Sequence
<220> FEATURE:
<223> OTHER INFORMATION: KEX2 leader sequence

<400> SEQUENCE: 9

Met Lys Trp Val Ser Phe Ile Ser Leu Leu Phe Leu Phe Ser Ser Ala
 1               5                  10                  15

Tyr Ser Arg Ser Leu Asp Lys Arg
```

-continued

```
            20


<210> SEQ ID NO 10
<211> LENGTH: 24
<212> TYPE: PRT
<213> ORGANISM: Artificial Sequence
<220> FEATURE:
<223> OTHER INFORMATION: KEX leader sequence

<400> SEQUENCE: 10

Met Lys Trp Val Ser Phe Ile Ser Leu Leu Phe Leu Phe Ser Ser Ala
 1               5                  10                  15

Tyr Ser Gly Ser Leu Asp Lys Arg
            20
```